(12) United States Patent
Okuma et al.

(10) Patent No.: US 9,580,702 B2
(45) Date of Patent: Feb. 28, 2017

(54) THERMOSTABLE CELLOBIOHYDROLASE AND AMINO ACID SUBSTITUTED VARIANT THEREOF

(71) Applicant: HONDA MOTOR CO., LTD., Minato-Ku, Tokyo (JP)

(72) Inventors: Jiro Okuma, Wako (JP); Asuka Yamaguchi, Wako (JP); Migiwa Suda, Wako (JP); Yoshitsugu Hirose, Wako (JP); Yasuhiro Kondo, Wako (JP); Tomohiko Kato, Kisarazu (JP); Daisuke Shibata, Kisarazu (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 14/644,604

(22) Filed: Mar. 11, 2015

(65) Prior Publication Data
US 2015/0259660 A1 Sep. 17, 2015

(30) Foreign Application Priority Data
Mar. 13, 2014 (JP) .................................. 2014-050084

(51) Int. Cl.
C12N 9/42 (2006.01)
C12P 19/02 (2006.01)
C12P 19/14 (2006.01)

(52) U.S. Cl.
CPC ............ C12N 9/2437 (2013.01); C12P 19/02 (2013.01); C12P 19/14 (2013.01); C12Y 302/01004 (2013.01)

(58) Field of Classification Search
None
See application file for complete search history.

(56) References Cited

FOREIGN PATENT DOCUMENTS

| JP | 2005-237233 A | 9/2005 |
| JP | 2006-515506 A | 6/2006 |
| JP | 2007-053994 A | 3/2007 |
| JP | 2008-193953 A | 8/2008 |
| JP | 2012-039967 A | 3/2012 |
| WO | 2004-016760 A2 | 2/2004 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession A9AWC6. Jan. 15, 2008.*
Accession G0FQP8. Oct. 19, 2011.*
Ganju et al., Purification and characterization of two cellobiohydrolases from *Chaetomium thermophile* var. coprophile, Biochimica et Biophysica Acta, 1989, vol. 993, pp. 266-274.
Hong et al., Cloning of a gene encoding thermostable cellobiohydrolase from Thermoascus aurantiacus and its expression in yeast, Appl Microbiol Biotechnol, 2003, vol. 63, pp. 42-50.
Zverlov et al., A newly described cellulosomal cellobiohydrolase, CelO, from Clostridium thermocellum: investigation of the exo-mode of hydrolysis, and binding capacity to crystalline cellulose, Microbiology, 2002, vol. 148, pp. 247-255.
Zverlov et al., Thermotoga neapolitana bglB gene, upstream of lamA, encodes a highly thermostable B-glucosidase that is a laminaribiase, Microbiology, 1997, vol. 143, pp. 3537-3542.
Kataeva et al., Cloning and Sequence Analysis of a New Cellulase Gene Encoding CelK, a Major Cellulosome Component of Clostridium thermocellum: Evidence for Gene Duplication and Recombination, Journal of Bacteriology, 1999, vol. 181, pp. 5288-5295.
Zhang et al., Characterization of a Thermomonospora fusca Exocellulase, Biochemistry, 1995, vol. 34, pp. 3386-3395.
Irwin et al., Cloning, expression and characterization of a Family 48 exocellulase, Cel48A, from Thermobifida fusca, Eur. J. Biochem., 2000, vol. 267, pp. 4988-4997.
Ruttersmith and Daniel, Thermostable cellobiohydrolase from the thermophilic eubacterium *Thermotoga* sp. strain FjSS3-B.1, Biochemical Journal, 1991, vol. 277, pp. 887-890.
Herai et al., Hyper-inducible expression system for streptomycetes, Proc. Natl. Acad. Sci. USA,2004, vol. 101, pp. 14031-14035.
Ogino et al., Over-expression system for secretory phospholipase D by Streptomyces lividans, Appl Microbiol Biotechnol, 2004, vol. 64, pp. 823-828.

(Continued)

*Primary Examiner* — Christian Fronda
(74) *Attorney, Agent, or Firm* — Carrie Blackman & Associates, P.C.; Joseph P. Carrier; Fulchand P. Shende

(57) ABSTRACT

A thermostable cellobiohydrolase including a cellobiohydrolase catalytic domain, the cellobiohydrolase catalytic domain including:
(A) a polypeptide including an amino acid sequence represented by SEQ ID NO: 1;
(B) a polypeptide including an amino acid sequence obtained by deletion, substitution or addition of at least one amino acid of the amino acid sequence represented by SEQ ID NO: 1, and having at least a cellobiohydrolase activity under conditions of 75° C. and pH 5.5;
(C) a polypeptide including an amino acid sequence having at least 85% sequence identity with the amino acid sequence represented by SEQ ID NO: 1, and having at least a cellobiohydrolase activity under conditions of 75° C. and pH 5.5;
(D) a polypeptide including an amino acid sequence represented by SEQ ID NO: 3;
(E) a polypeptide including an amino acid sequence obtained by deletion, substitution or addition of at least one amino acid (with a proviso that cysteine residues at positions 291 and 296 in the amino acid sequence are excluded) of the amino acid sequence represented by SEQ ID NO: 3, and having at least a cellobiohydrolase activity under conditions of 75° C. and pH 5.5; or
(F) a polypeptide including an amino acid sequence (with a proviso that cysteine residues are present at positions 291 and 296) having at least 85% sequence identity with the amino acid sequence represented by SEQ ID NO: 3, and having at least a cellobiohydrolase activity under conditions of 75° C. and pH 5.5.

2 Claims, 9 Drawing Sheets

(56) References Cited

OTHER PUBLICATIONS

Tamura et al., Development of a Host-Vector System in *Rhodococcus* Species, J. Environmental Biotechnol, 2007, vol. 7, pp. 3-10.

Kanehisa, Toward Pathway Engineering: A New Database of Genetic and Molecular Pathways, Science & Technology Japan, 1996, No. 59, pp. 34-38, http://www.genome.jp/kegg/, retrived on May 11, 2011.

Hoff et al., Orphelia: predicting genes in metagenomic sequencing reads, Nucleic Acids Research, 2009, vol. 37, Web Server issue W101-W105.

Noguchi et al., MetaGeneAnnotator: Detecting Species-Specific Patterns of Ribosomal Binding Site for Precise Gene Prediction in Anonymous Prokaryotic and Phage Genomes, DNA Research, 2008, 15(6).

Finn et al., The Pfam protein families database, Nucleic Acids Research Database, 2010, vol. 38, pp. D211-D222.

Suzuki et al., Screening of a Mutant Plasmid with High Expression Efficiency of GC-Rich leuB Gene of an Extreme Thermophile, Thermus thermophilus, in *Escherichia coli*, J. Biochem, 1997, vol. 121, pp. 1031-1034.

\* cited by examiner

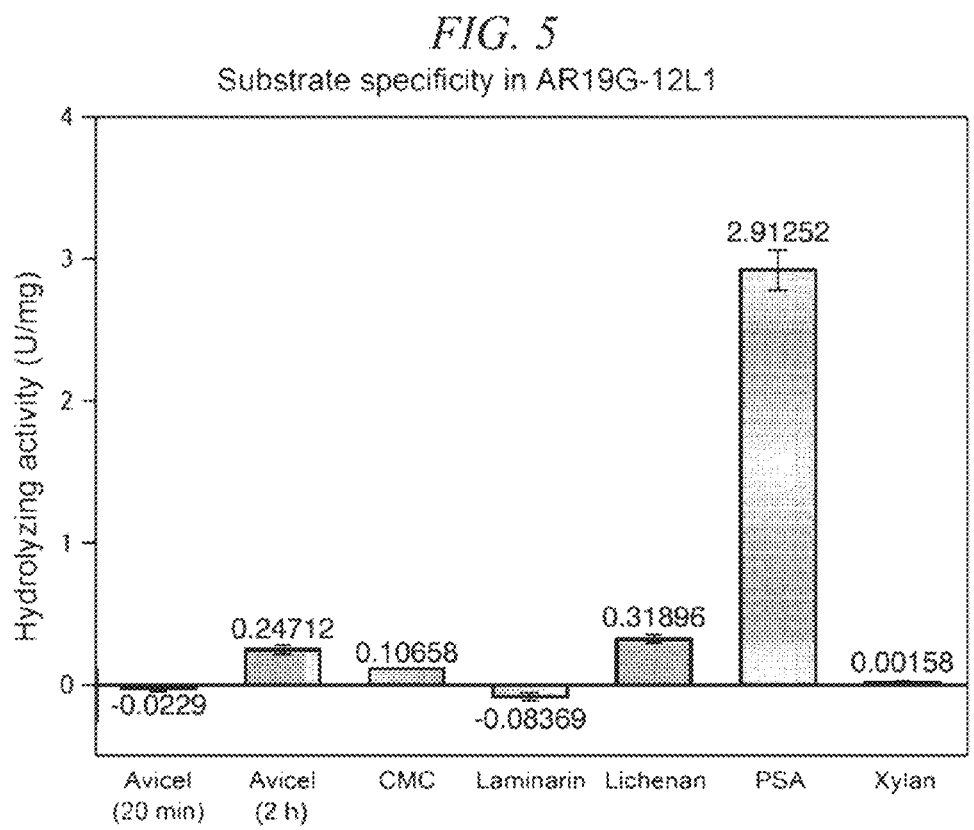
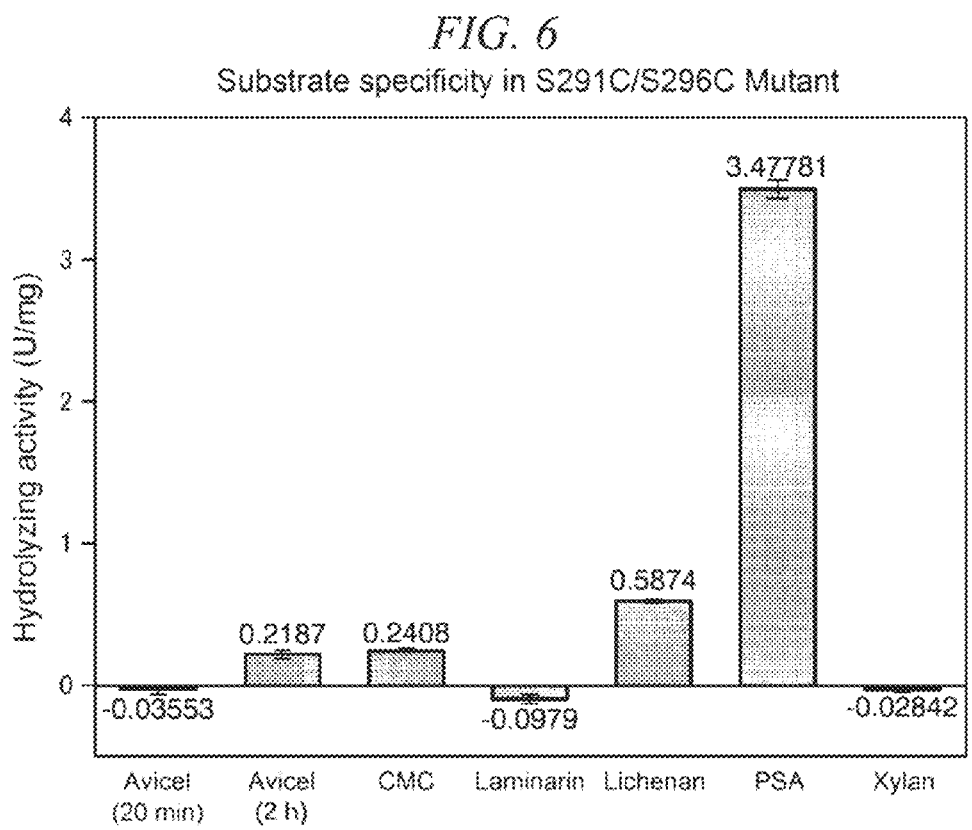

Temperature dependence in AR19G-12L1 activity pH dependence in AR19G-12L1 activity

THERMOSTABLE CELLOBIOHYDROLASE AND AMINO ACID SUBSTITUTED VARIANT THEREOF

BACKGROUND OF THE INVENTION

Field of the Invention

The present invention relates to thermostability of a cellobiohydrolase enzyme. A cellobiohydrolase is one of glycoside hydrolyzing enzymes involved in a process of hydrolyzing lignocellulose such as cellulose and hemicellulose and generating monosaccharides. More specifically, the present invention relates to a novel thermostable cellobiohydrolase, a polynucleotide encoding the aforementioned thermostable cellobiohydrolase, an expression vector for expressing the aforementioned thermostable cellobiohydrolase, a transformant into which the aforementioned expression vector has been incorporated and a method for producing a cellulose degradation product using the aforementioned thermostable cellobiohydrolase.

Priority is claimed on Japanese Patent Application No. 2014-050084, filed Mar. 13, 2014, the content of which is incorporated herein by reference.

Description of the Related Art

Plant biomass or lignocellulose is the most abundant renewable energy source on the earth and is expected as an alternative resource to petroleum. Main components of the biomass based on the dry weight are polysaccharides, such as cellulose and hemicellulose, and lignin. For example, polysaccharides are hydrolyzed to monosaccharides, such as glucose and xylose, by glycoside hydrolases collectively called as cellulase enzymes, and are then used as biofuels or materials for chemical products.

Lignocellulose having a complex structure is persistent and is difficult to degrade or hydrolyze with a single enzyme. For the complete degradation of lignocellulose, in general, three types of enzymes, i.e., an endoglucanase of glycoside hydrolase (cellulase or endo-1,4-β-D-glucanase, EC 3.2.1.4), an exo-type cellobiohydrolase (1,4-β-cellobiosidase or cellobiohydrolase. EC 3.2.1.91, EC 3.2.1.176), and a β-glucosidase (EC 3.2.1.21) are believed to be required. For the hydrolysis of lignocellulose, it is considered that appropriate formulation of multiple enzymes is necessary, including, in addition to the above, a xylanase serving as a hemicellulase (endo-1,4-β-xylanase, EC 3.2.1.8) or other plant cell wall degrading enzymes. On the other hand, it is thought that it is possible to significantly reduce the enzyme costs by using a thermostable enzyme and performing a lignocellulose hydrolysis process at a high temperature, thereby considerably reducing the enzyme amount and hydrolysis time. For this reason, for various cellulases, development of enzymes that are more excellent in terms of thermostability has been desired.

For thermophilic filamentous fungi that are eukaryotes, as compared with thermophilic bacteria and hyperthermophilic archaea that are prokaryotes, their threshold temperature for survival is as low as about 55° C. Therefore, in general, the thermostability of glycoside hydrolases expressed and secreted by thermophilic filamentous fungi is not so high. Cellobiohydrolases CBHI and CBHII of a thermophilic filamentous fungus *Chaetomium thermophilum* exhibit optimum temperatures of 750° and 70° C., respectively (for example, see Non-Patent Document 1), and a cellobiohydrolase CBHI of *Thermoascus aurantiacus* exhibits an optimum temperature of 65° C. (for example, see Non-Patent Document 2), which are the highest thermostability that has been reported so far for the cellobiohydrolases derived from filamentous fungi. Although there is a method of further improving the thermostability by substituting one or more amino acids in the cellobiohydrolase (for example, see Patent Document 1 or 2), the thermostability of the thus obtained mutant cellobiohydrolase is still at an insufficient level.

On the other hand, thermophiles growing at or above 55° C. and hyperthermophiles growing at or above 80° C. have been isolated and cultured from the extreme environments such as hot springs, hydrothermal vents, oil fields and mines. The majority of thermostable glycoside hydrolases derived from these thermophilic bacteria and hyperthermophilic archaea are enzymes with an endoglucanase activity, xylanase activity, xylosidase activity or glucosidase activity. Only a few cellobiohydrolases that play the most important role in the lignocellulose hydrolysis process have been isolated from three kinds of thermophilic bacteria belonging to the genera *Clostridium, Thermobifida* and *Thermotoga*. For example, a thermophilic anaerobic bacterium *Clostridium thermocellum* presents an enzyme complex cellulosome with a high lignocellulose hydrolytic activity extracellularly. The main enzymes of a cellulosome are cellobiohydrolases, and the three types thereof consisted of CelO belonging to GH5 family and CbhA and CelK belonging to GH9 family have been isolated, all of which have an optimum temperature ($T_{opt}$) of 60 to 65° C. (for example, see Non-Patent Documents 3 to 5). Two types of cellobiohydrolase genes; i.e., E3 belonging to GH6 family (for example, see Non-Patent Document 6) and Cel48A belonging to GH48 family (for example, see Non-Patent Document 7) have been isolated from a thermophilic actinomycete *Thermobifida fusca*. These cellobiohydrolases exhibit relatively high thermostability, exhibit a 50% activity of the maximum value within a temperature range from 40 to 60° C. and exhibit stable activity at 550° for at least 16 hours. However, these two types of cellobiohydrolases exhibit insufficient activity at 70° C. or higher, thus in the case of carrying out a hydrolysis process of cellulose by using these, the upper limit for the temperature of hydrolysis process will be from 60 to 65° C. It has been reported that a cellobiohydrolase derived from a thermophilic bacterium belonging to the genus *Thermotoga* exhibited the highest thermostability, with an optimum temperature ($T_{opt}$) of 105° C. and a half life of activity ($T_{half}$) of 70 minutes at 108° C. (for example, see Non-Patent Document 8). However, the above enzyme exhibits endoglucanase-like substrate specificity and exhibits a degradation activity only against amorphous cellulose and carboxymethyl cellulose (CMC). Further, since the hydrolytic activity of the filter paper is weak, efficient hydrolysis of crystalline lignocellulose by the above enzyme cannot be expected.

PRIOR ART DOCUMENTS

Patent Documents

[Patent Document 1] Published Japanese Translation No. 2006-515506 of the PCT International Publication
[Patent Document 2] Japanese Unexamined Patent Application, First Publication No. 2012-39967

Non-Patent Documents

[Non-Patent Document 1] Ganju et al., Biochim. Biophys. Acta. 1989, vol. 993, p. 266-274.
[Non-Patent Document 2] Hong et al., Appl Microbiol Biotechnol., 2003, vol. 63, p. 42-50.

[Non-Patent Document 3] Zverlov et al., Microbiology, 2002, vol. 148, p. 247-255.
[Non-Patent Document 4] Zverlov et al. Microbiology, 1997, vol. 143, p. 3537-3542.
[Non-Patent Document 5] Kataeva et al., Journal of Bacteriology, 1999, vol. 181, p. 5288-5295.
[Non-Patent Document 6] Zhang et al., Biochemistry, 1995, vol. 34, p. 3386-3395.
[Non-Patent Document 7] Irwin et al., Eur J Biochem., 2000, vol. 267, p. 4988-4997.
[Non-Patent Document 8] Ruttersmith and Daniel, Biochemical Journal, 1991, vol. 277, p. 887-890.

SUMMARY OF THE INVENTION

Problems to be Solved by the Invention

The present invention has an object of providing a novel thermostable cellobiohydrolase exhibiting at least a cellobiohydrolase activity at 75° C., a polynucleotide encoding the aforementioned thermostable cellobiohydrolase, an expression vector for expressing the aforementioned thermostable cellobiohydrolase, a transformant into which the aforementioned expression vector has been incorporated and a method for producing a cellulose degradation product using the aforementioned thermostable cellobiohydrolase.

Means for Solving the Problem

In order to solve the above problems, the inventors of the present invention have extracted DNA directly from the high temperature soil of hot springs and carried out a large-scale metagenomic sequencing of microbial flora that was difficult to culture, thereby succeeding in acquiring a thermostable cellobiohydrolase having a novel amino acid sequence to complete the present invention.

That is, as the thermostable cellobiohydrolase, polynucleotide, expression vector, transformant, method of producing a thermostable cellobiohydrolase, cellulase mixture and method for producing a cellulose degradation product according to the present invention, the following aspects [1] to [8] can be mentioned.

[1] A thermostable cellobiohydrolase including a cellobiohydrolase catalytic domain, the cellobiohydrolase catalytic domain including: (A) a polypeptide including an amino acid sequence represented by SEQ ID NO: 1; (B) a polypeptide including an amino acid sequence obtained by deletion, substitution or addition of at least one amino acid of the amino acid sequence represented by SEQ ID NO: 1, and having at least a cellobiohydrolase activity under conditions of 75° C. and pH 5.5; (C) a polypeptide including an amino acid sequence having at least 85% sequence identity with the amino acid sequence represented by SEQ ID NO: 1, and having at least a cellobiohydrolase activity under conditions of 75° C. and pH 5.5; (D) a polypeptide including an amino acid sequence represented by SEQ ID NO: 3; (E) a polypeptide including an amino acid sequence obtained by deletion, substitution or addition of at least one amino acid (with a proviso that cysteine residues at positions 291 and 296 in the amino acid sequence prior to the deletion, substitution or addition of at least one amino acid are excluded) of the amino acid sequence represented by SEQ ID NO: 3, and having at least a cellobiohydrolase activity under conditions of 75° C. and pH 5.5; or (F) a polypeptide including an amino acid sequence (with a proviso that cysteine residues are present at positions 291 and 296) having at least 85% sequence identity with the amino acid sequence represented by SEQ ID NO: 3, and having at least a cellobiohydrolase activity under conditions of 75° C. and pH 5.5.

[2] A polynucleotide including a region encoding a cellobiohydrolase catalytic domain, the region including: (a) a nucleotide sequence encoding a polypeptide including an amino acid sequence represented by SEQ ID NO: 1; (b) a nucleotide sequence encoding a polypeptide including an amino acid sequence obtained by deletion, substitution or addition of at least one amino acid of the amino acid sequence represented by SEQ ID NO: 1, and having at least a cellobiohydrolase activity under conditions of 75° C. and pH 5.5; (c) a nucleotide sequence encoding a polypeptide including an amino acid sequence having at least 85% sequence identity with the amino acid sequence represented by SEQ ID NO: 1, and having at least a cellobiohydrolase activity under conditions of 75° C. and pH 5.5; (d) a nucleotide sequence encoding a polypeptide including an amino acid sequence represented by SEQ ID NO: 3; (e) a nucleotide sequence encoding a polypeptide including an amino acid sequence obtained by deletion, substitution or addition of at least one amino acid (with a proviso that cysteine residues at positions 291 and 296 in the amino acid sequence prior to the deletion, substitution or addition of at least one amino acid are excluded) of the amino acid sequence represented by SEQ ID NO: 3, and having at least a cellobiohydrolase activity under conditions of 75° C. and pH 5.5; (f) a nucleotide sequence encoding a polypeptide including an amino acid sequence (with a proviso that cysteine residues are present at positions 291 and 296) having at least 85% sequence identity with the amino acid sequence represented by SEQ ID NO: 3, and having at least a cellobiohydrolase activity under conditions of 75° C. and pH 5.5; (g) a nucleotide sequence having at least 75% sequence identity with a nucleotide sequence represented by SEQ ID NO: 2 or 4, and encoding a polypeptide having at least a cellobiohydrolase activity under conditions of 75° C. and pH 5.5; or (h) a nucleotide sequence which is a nucleotide sequence of a polynucleotide hybridizing with a polynucleotide composed of a nucleotide sequence represented by SEQ ID NO: 2 or 4 under a stringent condition, and is encoding a polypeptide having at least a cellobiohydrolase activity under conditions of 75° C. and pH 5.5.

[3] An expression vector obtained by incorporating the polynucleotide according to the aforementioned aspect [2] and capable of expressing a polypeptide having at least a cellobiohydrolase activity under conditions of 75° C. and pH 5.5 in a host cell.

[4] A transformant obtained by introducing the expression vector according to the aforementioned aspect [3].

[5] The transformant according to the aforementioned aspect [4] which is a eukaryotic microbe.

[6] A method of producing a thermostable cellobiohydrolase, the method including producing a thermostable cellobiohydrolase in the transformant according to the aforementioned aspect [4] or [5].

[7] A cellulase mixture including: the thermostable cellobiohydrolase according to the aforementioned aspect [1], a thermostable cellobiohydrolase encoded by the polynucleotide according to the aforementioned aspect [2] or a thermostable cellobiohydrolase produced by the method of producing a thermostable cellobiohydrolase according to the aforementioned aspect [6]; and at least one other cellulase.

[8] A method of producing a cellulose degradation product including producing a cellulose degradation product by bringing a material containing cellulose into contact with the thermostable cellobiohydrolase according to the aforementioned aspect [1], a thermostable cellobiohydrolase encoded by the polynucleotide according to the aforementioned aspect [2], the transformant according to the aforementioned aspect [4] or [5], or a thermostable cellobiohydrolase produced by the method of producing a thermostable cellobiohydrolase according to the aforementioned aspect [6].

Effects of the Invention

A thermostable cellobiohydrolase according to the present invention at least has a cellobiohydrolase activity under conditions of 75° C. and pH 5.5. For this reason, the aforementioned thermostable cellobiohydrolase is suitable for a hydrolysis process of cellulose in high temperature conditions (for example, from 50 to 90° C.).

In addition, the polynucleotide, the expression vector into which the aforementioned polynucleotide has been incorporated and the transformant into which the aforementioned expression vector has been introduced according to the present invention are suitably used for the production of the thermostable cellobiohydrolase according to the present invention.

BRIEF DESCRIPTION OF THE DRAWINGS

FIG. 1 is an amino acid sequence alignment diagram of a catalytic domain of an amino acid sequence deduced from open reading frames AR19G-166 and AR19G-12, and amino acid sequences of a GH6 cellobiohydrolase (Genbank: ABX04776.1) of a mesophilic aerobic bacterium *Herpetosiphon aurantiacus* belonging to the phylum *Chloroflexi* and a GH6 cellobiohydrolase TfCel6B (GenBank: AAA62211.1) of a thermophilic soil actinomycete *Thermobifida fusca*.

FIG. 3 is an amino acid sequence alignment diagram of an amino acid sequence of a catalytic domain (AR19G-12L1, gene) from position 268 to position 315 of the open reading frame AR19G-12, the open reading frame AR19G-166 corresponding to the aforementioned partial sequence, and 35 types of GH6 cellobiohydrolases derived from bacteria.

FIG. 5 is a diagram showing the measurement results of the cellobiohydrolase activity of the AR19G-12L1 protein expressed in *E. coli* in Example 1 for each substrate.

FIG. 6 is a diagram showing the measurement results of the cellobiohydrolase activity of the amino acid substituted variants S291C/S296C proteins expressed in *E. coli* in Example 1 for each substrate.

DETAILED DESCRIPTION OF THE INVENTION

[Thermostable Cellobiohydrolase]

Figure 2:
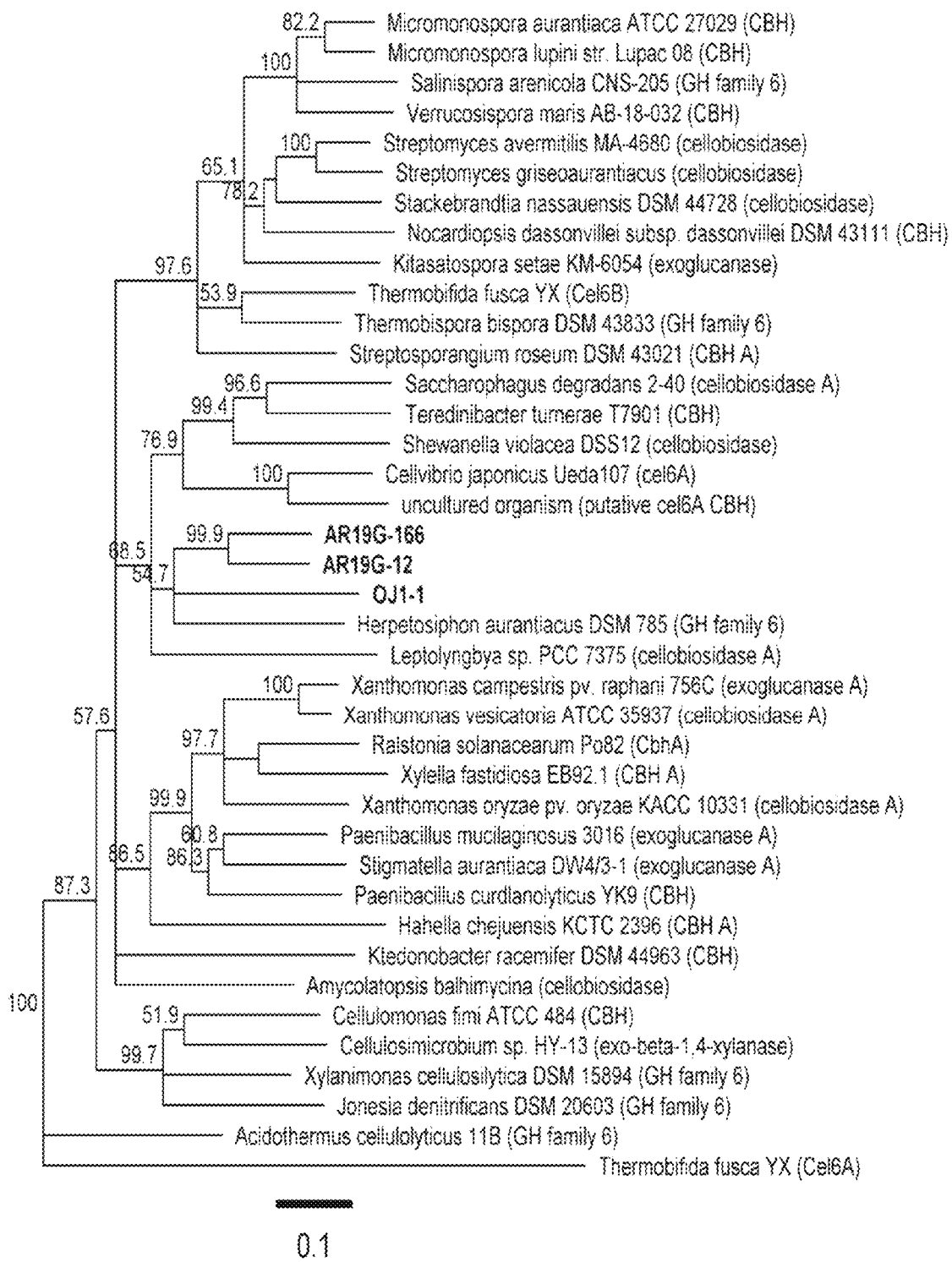
FIG. 2 is a rooted molecular phylogenetic tree based on the amino acid sequences of four open reading frames AR19G-166, AR19G-12 (OJ1-2) and OJ1-1 belonging to GH6 family which were obtained by a metagenomic analysis, as well as catalytic domains of 35 types of GH6 cellobiohydrolases derived from bacteria, and it has been drawn with a GH6 endoglucanase Cel6A of *Thermobifida fusca* as an outgroup. Since the amino acid sequence of OJ1-2 is 100% identical to that of AR19-12, it is presumed to be the same gene as AR19G-12, which is a partial sequence of AR19G-12.

Many microorganisms including filamentous fungi, bacteria and archaea are difficult to culture, and about 99% of the microorganisms inhabiting the microbial environments such as soil is said to be unknown microbes. In particular, the culturing of microorganisms living in a high temperature environment is extremely difficult, and it is thought that merely 0.1% or less of the microorganisms living in the soil is isolated and cultured with the currently available microbial culturing techniques. This difficulty in culturing the microorganisms in high temperature soil is one of the reasons why the development of thermostable cellobiohydrolases does not advance.

In recent years, by the development of next generation giga sequencer that enables a large amount of sequencing of giga base pairs, it is possible to entirely read the genome of the microbial flora included in the soil or the like. By using this analysis technique, a metagenome analysis method for reconstructing the genomic sequence of the microbial flora has been proposed by preparing the genomic DNA of the microbial populations from the environmental samples such as soil, directly and comprehensively reading the genomes of populations with non-uniform and miscellaneous genome organizations and assembling the decoded data by a parallel computer to thereby rapidly advancing the genome sequencing of the microorganisms that are difficult to culture.

The inventors of the present invention have, as shown in the following Example 1, obtained 44 open reading frames (ORF) encoding the amino acid sequences similar to (that is, having 20% or higher identity with, and Expectation value (i.e. E-value) is less than 1 e$^{-20}$) the known cellobiohydrolase enzymes by extracting the genomic DNA (metagenomic DNA) of the microbial population from the high temperature hot spring soil collected from five locations in Japan (for example, spring water of 50 to 98° C. that contains soil, mud, microbial mats, biofilms and the like may be mentioned) and carrying out the shotgun sequencing and annotation of the metagenomic DNA. Primers were designed based on the nucleotide sequence information of these ORFs, and the gene candidates were cloned from the hot spring soil metagenomic DNA by the PCR method. The DNA cloned by PCR was incorporated into *E. coli* to express a protein encoded by the aforementioned nucleotide sequence, and the functional screening by phosphoric acid swollen Avicel (PSA) degrading activity and carboxymethyl cellulose (CMC) degrading activity assay was carried out. A thermostable cellobiohydrolase AR19G-12L1 having the Avicel and PSA hydrolytic activity was obtained from the open reading frame AR19G-12 by PCR cloning to be described later. AR19G-12L1 is constituted of a full-length GH6 catalytic domain, and the amino acid sequence and nucleotide sequence thereof are represented by SEQ ID NO: 1 and SEQ ID NO: 2, respectively.

As shown in the following Example 1, AR9G-12L1 exhibits a high hydrolytic activity against water-soluble PSA, and also exhibits degradation activities against lichenan composed of β-1,3- and β-1,4 glucan and crystalline cellulose Avicel, but hardly exhibits degradation activities against CMC, laminarin composed of β-1,3- and β-1,6 glucan, and xylan. From this substrate specificity, AR19G-12L1 is suggested to be a cellobiohydrolase belonging to GH16 family.

In addition, when the amino acid sequence of AR19G-12L1 was searched against the database of known amino acid sequences, the amino acid sequence that showed the highest sequence identity was that of a glycoside hydrolase (SEQ ID NO: 8) belonging to GH6 family from a known mesophilic aerobic bacterium *Herpetosiphon aurantiacus* DSM 785 belonging to the phylum *Chloroflexi*, and the sequence identity (homology) was only 63%. From the substrate specificity and the sequence identity of the amino acid sequence with that of a known cellobiohydrolase, it is clear that AR19G-12L1 is a novel cellobiohydrolase belonging to GH16 family.

AR19G-12L1 has at least a cellobiohydrolase activity under conditions of 75° C. and pH 5.5. In fact, as shown in the following section <12> in Example 1, AR19G-12L1 shows a cellobiohydrolase activity within a wide temperature range from 40 to 90° C. More specifically, the cellobiohydrolase activity of AR19G-12L increases as the temperature increases in the range from 30 to 70° C., and the cellobiohydrolase activity tends to decrease as the temperature increases in the range from 70 to 100° C.

Just like AR19G-12L1, AR19G-12L1-S291C/S296C (hereinafter, may simply be referred to as "S291C/S296C") which is an amino acid substituted variant obtained by substituting the serine residues (S) at positions 291 and 296 in the amino acid sequence of AR19G-12L1 with cysteine residues (C) also has at least a cellobiohydrolase activity under conditions of 75° C. and pH 5.5. The amino acid sequence of the amino acid substituted variant S291C/S296C and the nucleotide sequence encoding the same are represented by SEQ ID NO: 3 and SEQ ID NO: 4, respectively. In fact, as shown in the following section <12> in Example 1, S291C/S296C shows a cellobiohydrolase activity within a wide temperature range from 40 to 100° C. More specifically, the cellobiohydrolase activity of S291C/S296C increases as the temperature increases in the range from 30 to 75° C., the cellobiohydrolase activity tends to decrease as the temperature increases in the range from 75 to 85° C., and the cellobiohydrolase activity does not reduce and remains almost the same in the range from 85 to 100° C. In other words, the amino acid substituted variant S291C/S296C is very excellent in thermostability than AR19G-12L1.

It should be noted that in the present specification, the expression "having an activity" means that a significant difference occurs in the hydrolyzed amount of reducing ends or the color reaction for at least one substrate as compared to the negative control.

In general, a protein having any physiological activity can be deleted of, substituted by or added with at least one amino acid without impairing the physiological activity. In other words, AR19G-12L1 or its amino acid substituted variant S291C/S296C can also be deleted of, substituted by or added with at least one amino acid without losing the cellobiohydrolase activity.

That is, the thermostable cellobiohydrolase according to the present invention is a thermostable cellobiohydrolase having a cellobiohydrolase catalytic domain (i.e., a polypeptide including the amino acid sequences required to have a cellobiohydrolase activity) composed of any one of the following (A) to (F):

(A) a polypeptide including an amino acid sequence represented by SEQ ID NO: 1;

(B) a polypeptide including an amino acid sequence obtained by deletion, substitution or addition of at least one amino acid of the amino acid sequence represented by SEQ ID NO: 1, and having at least a cellobiohydrolase activity under conditions of 75° C. and pH 5.5;

(C) a polypeptide including an amino acid sequence having at least 85% sequence identity with the amino acid sequence represented by SEQ ID NO: 1, and having at least a cellobiohydrolase activity under conditions of 75° C. and pH 5.5;

(D) a polypeptide including an amino acid sequence (an amino acid sequence obtained by substituting both of the serine residue at position 291 and serine residue at position 296 with cysteine residues in the amino acid sequence represented by SEQ ID NO: 1) represented by SEQ ID NO: 3:

(E) a polypeptide including an amino acid sequence obtained by deletion, substitution or addition of at least one amino acid (with a proviso that cysteine residues at positions 291 and 296 in the amino acid sequence prior to the deletion, substitution or addition of at least one amino acid are excluded) of the amino acid sequence represented by SEQ ID NO: 3, and having at least a cellobiohydrolase activity under conditions of 75° C. and pH 5.5; or (F) a polypeptide including an amino acid sequence (with a proviso that cysteine residues are present at positions 291 and 296) having at least 85% sequence identity with the amino acid sequence represented by SEQ ID NO: 3, and having at least a cellobiohydrolase activity under conditions of 75° C. and pH 5.5.

In the aforementioned polypeptides (B) and (E), the number of amino acids deleted or substituted in or added to the amino acid sequence represented by SEQ ID NO: 1 or 3 is preferably from 1 to 20, more preferably from 1 to 10, and still more preferably from 1 to 5.

In the aforementioned polypeptides (C) and (F), the sequence identity with the amino acid sequence represented by SEQ ID NO: 1 or 3 is not particularly limited as long as it is 85% or higher, although it is preferably 90% or higher and more preferably 95% or higher.

It should be noted that the sequence identity (homology) between amino acid sequences is obtained, as a percentage of matched amino acids with respect to the amino acid sequence as a whole except for the gaps in the resulting alignment, by juxtaposing two amino acid sequences so as to coincide the corresponding amino acids as many as possible, while adding a gap into a portion that corresponds to the insertion and deletion. The sequence identity between amino acid sequences can be determined using a variety of known homology search software in the aforementioned technical field. The sequence identity values of the amino acid sequences in the present invention are obtained by calculation based on the alignment obtained by known homology search software BLASTP.

The aforementioned polypeptides (B), (C), (E) and (F) may be those that are artificially designed, or may be homologues of AR19G-12L1 and the like or partial proteins thereof.

Each of the aforementioned polypeptides (A) to (F) may be synthesized chemically based on the amino acid sequence or may be produced by a protein expression system using the polynucleotide according to the present invention to be described later. In addition, each of the aforementioned polypeptides (B), (C), (E) and (F) can also be artificially synthesized using a genetic recombination technique for introducing an amino acid mutation based on the polypeptide composed of the amino acid sequence represented by SEQ ID NO: 1 or 3.

The aforementioned polypeptides (A) to (F) has at least a cellobiohydrolase activity under conditions of 75° C. and pH 5.5. For this reason, by including any one of the aforementioned polypeptides (A) to (F) as a catalytic domain of cellobiohydrolase, a thermostable cellobiohydrolase can be obtained. Among these, it is preferable to include any one of the aforementioned polypeptides (D) to (F) as a catalytic domain of cellobiohydrolase since they exhibit a very high cellobiohydrolase activity even at 70 to 100° C.

The thermostable cellobiohydrolase according to the present invention use PSA as a substrate. The aforementioned thermostable cellobiohydrolase may use another type of β-glucan other than PSA as a substrate. As the another type of β-glucan, for example, Lichenan composed of β-1,3 bonds and β-1,4 bonds, crystalline celluloses such as Avicel, crystalline bacterial cellulose (Bacterial microcrystalline cellulose, BMCC) and filter papers, carboxymethylcellulose (CMC), glucans composed of β-1,3 bonds and β-1,6 bonds, glucans composed of β-1,3 bonds, glucans composed of β-1,6 bonds, xylan and the like can be mentioned. As the thermostable cellobiohydrolase according to the present invention, those using at least one of glucans composed of β-1,3 bonds and β-1,4 bonds and crystalline cellulose, in addition to PSA, as substrates are preferred, and those using PSA, glucans composed of β-1,3 bonds and β-1,4 bonds and crystalline cellulose as substrates are more preferred.

The optimum pH of the thermostable cellobiohydrolase according to the present invention is in the pH range of 4.0 to 6.5, although it varies depending on the reaction temperature. As the thermostable cellobiohydrolase according to the present invention, those exhibiting a cellobiohydrolase activity at least in the pH range of 5.0 to 7.0 are preferred, and those exhibiting a cellobiohydrolase activity in the pH range of 4.0 to 7.0 are more preferred.

The thermostable cellobiohydrolase according to the present invention may have a cellulose hydrolytic activity other than the cellobiohydrolase activity. Examples of other cellulose hydrolytic activities include an endoglucanase activity, xylanase activity and β-glucosidase activity.

The thermostable cellobiohydrolase according to the present invention may be an enzyme composed only of a cellobiohydrolase catalytic domain including any one of the aforementioned polypeptides (A) to (F), or may include other domains. Examples of other domains include a domain other than the cellobiohydrolase catalytic domain present in the known cellobiohydrolases. For example, in the thermostable cellobiohydrolase according to the present invention, enzymes obtained by replacing the cellobiohydrolase catalytic domain of the known cellobiohydrolase with the aforementioned polypeptides (A) to (F) are also included.

In those cases where the thermostable cellobiohydrolase according to the present invention include a domain other than the cellobiohydrolase catalytic domain, it is preferable to include a cellulose binding module. The cellulose binding module may be present upstream (N-terminal side) or may be present downstream (C-terminal side) of the cellobiohydrolase catalytic domain. In addition, the cellulose binding module and the cellobiohydrolase catalytic domain may be linked directly or may be linked via a linker domain with an appropriate length. As the thermostable cellobiohydrolase according to the present invention, those in which a cellulose binding module is present upstream or downstream of the cellobiohydrolase catalytic domain via a linker domain are preferred, and those in which a cellulose binding module is present upstream of the cellobiohydrolase catalytic domain via a linker domain are more preferred.

The cellulose binding module included in the thermostable cellobiohydrolase according to the present invention may be a domain having the ability to bind to cellulose, for example, the ability to bind to PSA and crystalline Avicel, and the amino acid sequence thereof is not particularly limited. As the aforementioned cellulose binding module, for example, the cellulose binding module present in the known proteins or those obtained after appropriate modification may be used. In addition, in those cases where the thermostable cellobiohydrolase according to the present invention include the cellobiohydrolase catalytic domain and a cellulose binding module, it is preferable that these are bonded via a linker sequence. The amino acid sequence and its length or the like of the aforementioned linker sequence is not particularly limited.

In addition, the thermostable cellobiohydrolase according to the present invention may have, at the N-terminus or C-terminus, a signal peptide allowed to migrate to a particular region within the cell to be localized or a signal peptide secreted to the outside of the cell. Examples of such signal peptides include an apoplast migrating signal peptide, an endoplasmic reticulum retention signal peptide, a nuclear migrating signal peptide and a secretion-type signal peptide. As an endoplasmic reticulum retention signal peptide, for example, there is a signal peptide including an amino acid sequence HDEL, or the like.

Moreover, in addition to the above, for example, at the N-terminus or C-terminus, various tags may be added to the thermostable cellobiohydrolase according to the present invention in order to enable a simple purification when it is produced using an expression system. As the tag, for example, it is possible to use a tag that is widely used in the expression and purification of recombinant proteins, such as His tags, HA (hemagglutinin) tags, Myc tags and Flag tags.

[Polynucleotide Encoding Thermostable Cellobiohydrolase]

A polynucleotide according to the present invention encodes the thermostable cellobiohydrolase according to the present invention. By introducing an expression vector into which the aforementioned polynucleotide has been incorporated into a host, the aforementioned thermostable cellobiohydrolase can be produced using an expression system of the aforementioned host.

More specifically, the polynucleotide according to the present invention is a polynucleotide encoding a region including a cellobiohydrolase catalytic domain composed of any one of the following nucleotide sequences (a) to (h):
(a) a nucleotide sequence encoding a polypeptide composed of an amino acid sequence represented by SEQ ID NO: 1;
(b) a nucleotide sequence encoding a polypeptide composed of an amino acid sequence obtained by deletion, substitution or addition of at least one amino acid of the amino acid sequence represented by SEQ ID NO: 1, and having at least a cellobiohydrolase activity under conditions of 75° C. and pH 5.5;

(c) a nucleotide sequence encoding a polypeptide composed of an amino acid sequence having at least 85% sequence identity with the amino acid sequence represented by SEQ ID NO: 1, and having at least a cellobiohydrolase activity under conditions of 75° C. and pH 5.5;
(d) a nucleotide sequence encoding a polypeptide composed of an amino acid sequence represented by SEQ ID NO: 3;
(e) a nucleotide sequence encoding a polypeptide composed of an amino acid sequence obtained by deletion, substitution or addition of at least one amino acid (with a proviso that cysteine residues at positions 291 and 296 in the amino acid sequence prior to the deletion, substitution or addition of at least one amino acid are excluded) of the amino acid sequence represented by SEQ ID NO: 3, and having at least a cellobiohydrolase activity under conditions of 75° C. and pH 5.5;
(f) a nucleotide sequence encoding a polypeptide composed of an amino acid sequence (with a proviso that cysteine residues are present at positions 291 and 296) having at least 85% sequence identity with the amino acid sequence represented by SEQ ID NO: 3, and having at least a cellobiohydrolase activity under conditions of 75° C. and pH 5.5;
(g) a nucleotide sequence having at least 75% sequence identity with a nucleotide sequence represented by SEQ ID NO: 2 or 4, and encoding a polypeptide having at least a cellobiohydrolase activity under conditions of 75° C. and pH 5.5; or
(h) a nucleotide sequence which is a nucleotide sequence of a polynucleotide hybridizing with a polynucleotide composed of a nucleotide sequence represented by SEQ ID NO: 2 or 4 under a stringent condition, and is encoding a polypeptide having at least a cellobiohydrolase activity under conditions of 75° C. and pH 5.5.

It should be noted that in the present invention and in the present specification, the term "stringent condition" refers to, for example, a method described in Molecular Cloning—A LABORATORY MANUAL THIRD EDITION (Sambrook et al., Cold Spring Harbor Laboratory Press). For example, a condition for hybridization by incubating several hours to overnight at 42 to 70° C. in a hybridization buffer composed of 6×SSC (composition of 20×SSC: 3M sodium chloride, 0.3M citric acid solution, pH 7.0), 5×Denhardt's solution (composition of 100 Denhardt's solution: 2% by mass bovine serum albumin, 2% by mass Ficoll, 2% by mass polyvinylpyrrolidone), 0.5% by mass of SDS, 0.1 mg/mL salmon sperm DNA and 50% formamide can be mentioned. It should be noted that as a washing buffer used in the washing after incubation, a 0.1% by mass SDS-containing 1×SSC solution is preferred, and a 0.1% by mass SDS-containing 0.1×SSC solution is more preferred.

In the aforementioned nucleotide sequences (a) to (f), it is preferable to select a degenerate codon which has a high codon usage in the host. For example, the aforementioned nucleotide sequence (a) may be a nucleotide sequence represented by SEQ ID NO: 2, or may be a nucleotide sequence obtained by modifying the nucleotide sequence represented by SEQ ID NO: 2 to more frequently used codons in a host without changing the amino acid sequence encoded. It should be noted that the aforementioned nucleotide sequence (d) may be a nucleotide sequence represented by SEQ ID NO: 2, or may be a nucleotide sequence obtained by modifying the nucleotide sequence represented by SEQ ID NO: 4 to more frequently used codons in a host without changing the amino acid sequence encoded. The modification of codons can be carried out by a known genetic engineering technique.

A polynucleotide composed of the nucleotide sequence represented by SEQ ID NO: 2 or 4 may be synthesized chemically based on the nucleotide sequence information, or may be the full length of genes encoding AR19G-12 (may be referred to as an "AR19G-12 gene") or partial regions containing a cellobiohydrolase catalytic domain obtained from nature by a genetic recombination technique. The full length of the AR19G-12 gene or the partial region thereof can be obtained, for example, by collecting a sample containing microorganisms from nature and carrying out PCR using a genomic DNA that has been recovered from the aforementioned sample as a template and using forward and reverse primers designed by a conventional method based on the nucleotide sequence represented by SEQ ID NO: 2 or 4. The cDNA synthesized by a reverse transcription reaction using the mRNA recovered from the aforementioned sample as a template may be used as a template. It should be noted that a sample for recovering a nucleic acid to serve as a template is preferably a sample collected from a high temperature environment such as hot spring soil (for example, spring water of 50 to 98° C. that contains soil, mud, microbial mats, biofilms and the like).

In the aforementioned nucleotide sequence (g), the sequence identity with the nucleotide sequence represented by SEQ ID NO: 2 or 4 is not particularly limited as long as it is at least 75%, but is preferably at least 80%, more preferably at least 85%, still more preferably at least 90%, and still more preferably at least 95%.

It should be noted that the sequence identity (homology) between nucleotide sequences is obtained, as a percentage of matched nucleotides with respect to the nucleotide sequence as a whole except for the gaps in the resulting alignment, by juxtaposing two nucleotide sequences so as to coincide the corresponding nucleotides as many as possible, while adding a gap into a portion that corresponds to the insertion and deletion. The sequence identity between nucleotide sequences can be determined using a variety of known homology search software in the aforementioned technical field. The sequence identity values of the nucleotide sequence in the present invention are obtained by calculation based on the alignment obtained by known homology search software BLASTN.

For example, each of the polynucleotides composed of the aforementioned nucleotide sequence (b), (c), (e) or (t) can be artificially synthesized by the deletion, substitution or addition of at least one nucleotide with respect to a polynucleotide composed of the nucleotide sequence represented by SEQ ID NO: 2 or 4. In addition, the aforementioned nucleotide sequence (b), (c), (e) or (f) may be a full length sequence of a homologous gene of AR19G-12 gene or the partial sequence thereof. A homologous gene of AR19G-12 gene can be obtained by a gene recombination technique used when obtaining a homologous gene of genes with a known nucleotide sequence.

The polynucleotide according to the present invention may be those having only a region encoding a cellobiohydrolase catalytic domain, or may have a region encoding a cellulose binding module, a linker sequence, various signal peptides, various tags, and the like, in addition to the aforementioned region.

[Expression Vector]

An expression vector according to the present invention is an expression vector to which the aforementioned polynucleotide according to the present invention has been incorporated and capable of expressing a polypeptide having at least a cellobiohydrolase activity under conditions of 75° C. and pH 5.5 in a host cell. That is, it is an expression vector into which the aforementioned polynucleotide according to the present invention has been incorporated in a state capable of expressing the aforementioned thermostable cellobiohydrolase according to the present invention. More specifically, it is necessary to be incorporated into an expression vector as an expression cassette composed of, from the upstream, DNA having a promoter sequence, the aforementioned polynucleotide according to the present invention and DNA having a terminator sequence. It should be noted that incorporation of the polynucleotide into an expression vector can be carried out by using a known genetic recombination technique, and it is also possible to use a commercially available expression vector preparation kit.

The aforementioned expression vector may be those to be introduced into prokaryotic cells such as E. coli, or may be those to be introduced into eukaryotic cells, such as yeast, filamentous fungi, cultured insect cells, cultured mammalian cells and plant cells. As these expression vectors, an arbitrary expression vector which is generally used in accordance with the respective host can be used.

The expression vector according to the present invention is preferably an expression vector into which not only the aforementioned polynucleotide according to the present invention but also a drug resistance gene and the like have been incorporated. This is because it is possible to easily perform a selection between a transformed host and a non-transformed host by the expression vector.

Examples of the aforementioned drug resistance gene include a kanamycin resistance gene, a hygromycin resistance gene and a bialaphos resistance gene.

[Transformant]

The expression vector according to the present invention has been introduced into a transformant according to the present invention. In the aforementioned transformant, the thermostable cellobiohydrolase according to the present invention can be expressed. The current host range is narrow, that is, the heterologous expression is difficult for many of the conventionally known cellobiohydrolases. On the other hand, the thermostable cellobiohydrolase according to the present invention can be expressed in a wide range of expression hosts, such as E. coli, yeast, filamentous fungi, and higher plant chloroplasts. That is, the transformant according to the present invention is E. coli, yeast, filamentous fungi, higher plant chloroplast or the like into which the expression vector according to the present invention has been introduced.

A method using an expression vector to produce a transformant is not particularly limited, and it can be carried out by a method commonly used in the case of producing a transformant. As the aforementioned method, for example, an Agrobacterium-mediated method, a particle gun method, an electroporation method, a PEG (polyethylene glycol) method and the like can be mentioned. Of these, in those cases where the host is a plant cell, it is preferably carried out by the particle gun method or the Agrobacterium-mediated method.

As another aspect, the host for introducing an expression vector may be prokaryotic cells, such as E. coli, or may be eukaryotic cells, such as yeast, filamentous fungi, cultured insect cells, cultured mammalian cells and plant cells. By culturing a transformant of E. coli, the thermostable cellobiohydrolase according to the present invention can be produced more easily and in large quantities. On the other hand, because proteins are glycosylated within the eukaryotic cells, by using a transformant of eukaryotic cells, it is possible to produce a thermostable cellobiohydrolase which is more excellent in thermostability than the case of using a transformant of prokaryotic cells. In particular, when the aforementioned transformant is a filamentous fungus, such as Aspergillus, or a eukaryotic microbe, such as a yeast, a thermostable cellobiohydrolase which is more excellent in thermostability can be produced in large quantities by a relatively simple manner.

Since a gene encoding the thermostable cellobiohydrolase according to the present invention has a high GC content, actinomycetes such as bacteria belonging to the genus Streptomyces are also preferred as a host for the expression. In particular, bacteria belonging to the genus Streptomyces have been known to produce useful antibiotics and physiologically active substances and are useful bacteria that are widely used from an industrial perspective. Overexpression systems of foreign genes that applying the ability to produce materials have been developed, and some successful examples have been reported (Herai, S. et al., Proc. Natl. Acad. Sci. USA, vol. 101, p. 14031-14035 (2004); Japanese Unexamined Patent Application, First Publication No. 2005-237233; Japanese Unexamined Patent Application, First Publication No. 2007-53994; Ogino, C. et al, Appl Microbiol Biotechnol vol. 64, 823-828 (2004): Japanese Unexamined Patent Application, First Publication No. 2008-193953; Tamura, T. et al, J. Environmental Biotechnol vol. 7, 3-10 (2007)). In particular, since actinomycetes have genomes of high GC content, expression of genes with a high GC content which is difficult to express in E. coli tends to be favorable (Tamura, T. et al., J. Environmental Biotechnol vol. 7, 3-10 (2007)), and extremely high levels of expression where the expression of heterologous protein reaching up to 40% of the actinomycete cell free extracts has also been reported (Herai, S. et al., Proc. Natl. Acad. Sci. USA, vol. 101, p. 14031-14035 (2004)).

When prokaryotic cells, yeast, filamentous fungi, cultured insect cells, cultured mammalian cells and the like are used as a host, in general, the resulting transformants can be cultured by a conventional method in the same manner as that of the host prior to the transformation.

When the transformant according to the present invention is a plant, as a host, a cultured plant cell may be used, or a plant organ or plant tissue may be used. By using a well-known plant tissue culture method and the like, it is possible to obtain a transformed plant from the transformed plant cells, callus, and the like. For example, a transformed plant can be obtained by culturing the transformed plant cells using a hormone-free regeneration medium and the like, and transplanting the obtained rooted seedling plants to soil and the like for growth.

[Production Method of Thermostable Cellobiohydrolase]

A method of producing a thermostable cellobiohydrolase according to the present invention is a method of producing a thermostable cellobiohydrolase in the aforementioned transformant according to the present invention. In a transformant produced using an expression vector into which the aforementioned polynucleotide according to the present invention has been incorporated downstream of a promoter which does not have the ability to control the timing of the expression and the like, the thermostable cellobiohydrolase according to the present invention is expressed constitutively. On the other hand, for the transformants that have been produced using the so-called expression inducible promoter to induce expression by a specific compound, temperature conditions or the like, by carrying out an induction treatment suitable for each of the expression inducing conditions, the thermostable cellobiohydrolase is expressed inside the aforementioned transformant.

A thermostable cellobiohydrolase produced by a transformant may be used in a state where it is remained inside the aforementioned transformant, or may be extracted and purified from the aforementioned transformant.

A method of extracting and purifying the thermostable cellobiohydrolase from the transformant is not particularly limited, as long as it is a method that does not impair the activity of the thermostable cellobiohydrolase, and extraction can be carried out by methods commonly used in the case of extracting a polypeptide from the cell or biological tissue. As the aforementioned method, for example, a method in which the transformant is immersed in a suitable extraction buffer to extract the thermostable cellobiohydrolase, followed by separation into an extraction liquid and solid residue can be mentioned. As the extraction buffer, those containing a solubilizing agent such as a surfactant are preferred.

When the transformant is a plant, the aforementioned transformant may be cut into small pieces or grinded prior to being immersed in the extraction buffer. In addition, as a method of separating the extraction liquid and the solid residue, for example, known solid-liquid separation treatments such as filtration methods, compression filtration methods and centrifugation methods can be used, or a transformant immersed in the extraction buffer may be squeezed. The thermostable cellobiohydrolase in the extraction liquid can be purified by known purification methods such as a salting-out method, ultrafiltration method and chromatography method.

In those cases where the thermostable cellobiohydrolase according to the present invention is expressed in a state of having a secretory signal peptide in a transformant, after culturing the transformant, it is possible to easily obtain a solution containing the thermostable cellobiohydrolase by collecting the culture solution supernatant obtained by removal of the transformant from the resulting culture. In addition, if the thermostable cellobiohydrolase according to the present invention has a tag such as His tag, by the affinity chromatography method using the aforementioned tag, it is possible to easily purify the thermostable cellobiohydrolase in the extraction liquid and culture supernatant.

One aspect of the method of producing a thermostable cellobiohydrolase according to the present invention is:
a method that includes producing a thermostable cellobiohydrolase inside a transformant;
the aforementioned transformant may be a transformant produced using an expression vector incorporated downstream of a promoter which does not have the ability to control the timing of the expression and the like, or may be a transformant produced using an expression inducible promoter;
and the aforementioned production method may further include extraction and purification of the thermostable cellobiohydrolase from the aforementioned transformant.

[Cellulase Mixture]

The aforementioned thermostable cellobiohydrolase according to the present invention or the thermostable cellobiohydrolase produced by the aforementioned method of producing a thermostable cellobiohydrolase according to the present invention can also be used as a cellulase mixture containing at least one other cellulase. The thermostable cellobiohydrolase produced by the aforementioned method for producing a thermostable cellobiohydrolase according to the present invention may be in a state of being included in the transformant, or may be those extracted and purified from the transformant. By using the thermostable cellobiohydrolase according to the present invention as a mixture with other cellulases for the degradation reaction of cellulose, it is possible to degrade persistent lignocellulose more efficiently.

Other cellulases other than the thermostable cellobiohydrolase contained in the above cellulase mixture are not particularly limited as long as they have a hydrolytic activity of cellulose. Examples thereof include β-glucosidase, endoglucanase and hemicellulases such as xylanase and β-xylosidase. As the cellulase mixture according to the present invention, those containing at least one of a hemicellulase and endoglucanase are preferred, and those containing both a hemicellulase and endoglucanase are more preferred. Among them, those containing at least one selected from the group consisting of xylanase, β-xylosidase, β-glucosidase and endoglucanase are preferred, and those containing all of xylanase, β-xylosidase, β-glucosidase and endoglucanase are more preferred.

Other cellulase contained in the above cellulase mixture is preferably a thermostable cellulase having at least a cellulase activity at 70° C., and more preferably a thermostable cellulase having a cellulase activity at 70 to 90° C. As a result of all the enzymes included in the above cellulase mixture being heat resistant (that is, the optimum temperature of the enzyme activity or the thermal denaturation temperature of the enzyme protein is 70° C. or higher), the degradation reaction of cellulose by the above cellulase mixture can be carried out efficiently under high temperature conditions. That is, when the above cellulase mixture contains only thermostable cellulases, by using the above cellulase mixture for the lignocellulose hydrolysis process, it becomes possible to carry out a lignocellulose hydrolysis reaction in a high temperature environment with a hydrolysis temperature of 70 to 90° C. (high temperature hydrolysis). By the high temperature hydrolysis, it is possible to significantly reduce the amount of enzyme and hydrolysis time, and the hydrolysis cost is greatly reduced.

[Production Method of Cellulose Degradation Product]

A method of producing a cellulose degradation product according to the present invention is a method to obtain a degradation product by degrading cellulose by the thermostable cellobiohydrolase according to the present invention. More specifically, a cellulose degradation product is produced by bringing a material containing cellulose into contact with the thermostable cellobiohydrolase according to the present invention, the transformant according to the present invention, or the thermostable cellobiohydrolase produced by the method of producing a thermostable cellobiohydrolase according to the present invention.

The term "cellulose degradation product" used herein refers mainly to cellobiose and other cellooligosaccharides including cellotriose and glucose.

The material containing cellulose is not particularly limited as long as it contains cellulose. As the above material, for example, cellulose-based biomass such as weeds and agricultural waste, waste paper and the like can be mentioned. The above material containing cellulose is preferably subjected to a physical treatment such as crushing and cutting into small pieces, chemical treatment using an acid, alkali, and the like, immersion or dissolution treatment in an appropriate buffer or the like, prior to being brought into contact with the thermostable cellobiohydrolase according to the present invention.

The reaction condition for the cellulose hydrolysis reaction by the thermostable cellobiohydrolase according to the present invention may be a condition under which the aforementioned thermostable cellobiohydrolase exhibits a cellobiohydrolase activity. For example, it is preferable to carry out the reaction at 55 to 100° C. with a pH of 3.5 to 7.0, and it is more preferable to carry out the reaction at 70 to 100° C. with a pH of 4.0 to 6.0. The reaction time is appropriately adjusted in consideration of the type, the method of pretreatment, the amount and the like of the material containing cellulose which is subjected to hydrolysis. The reaction can be carried out in a reaction time of 10 minutes to 100 hours, for example, and 1 to 100 hours when degrading the cellulose-based biomass.

For the hydrolysis reaction of cellulose, it is also preferable to use at least one other cellulase in addition to the thermostable cellobiohydrolase according to the present invention. As the above other cellulase, the same cellulase as those to be included in the aforementioned cellulase mixture can be used, and it is preferably a thermostable cellulase having at least a cellulase activity at 70° C. and more preferably at least at 70 to 100° C. In addition, for the aforementioned method of producing a cellulose degradation product, the aforementioned cellulase mixture may be used in place of the thermostable cellobiohydrolase according to the present invention, the transformant according to the present invention, or the thermostable cellobiohydrolase produced by the method of producing a thermostable cellobiohydrolase according to the present invention.

That is, one aspect of the method of producing a cellulose degradation product of the present invention includes:

a step of bringing a material containing cellulose into contact with the thermostable cellobiohydrolase according to the present invention, the transformant according to the present invention, the thermostable cellobiohydrolase produced by the method of producing a thermostable cellobiohydrolase according to the present invention, or the cellulase mixture containing the thermostable cellobiohydrolase according to the present invention, thereby producing a cellulose degradation product through the hydrolysis reaction of cellulose by the above thermostable cellobiohydrolase. In the above hydrolysis reaction, the reaction temperature is preferably from 55 to 100° C.; pH is preferably from 3.5 to 7.0; and the reaction time is preferably from 10 minutes to 100 hours.

Furthermore, the above production method may include a step of carrying out a physical treatment, chemical treatment, or immersion or dissolution treatment in a buffer, prior to bringing the aforementioned material containing cellulose into contact with the thermostable cellobiohydrolase according to the present invention.

EXAMPLES

Next, the present invention will be described in more detail based on a series of Examples, but the present invention is not limited to the following Examples.

Example 1

Cloning of a Novel Thermostable Cellobiohydrolase from Hot Spring Soil

<1> DNA Extraction from Hot Spring Soil and Whole Genome Sequence (WGS)

Soil DNA was collected from neutral to weakly alkaline hot springs for the sake of gene search of thermostable cellobiohydrolases (optimum temperature: 55° C. or higher) and extremely thermostable cellobiohydrolases (optimum temperature: 80° C. or higher), and the sequencing of metagenomic DNA of the microbial flora that make up these soil was carried out.

As neutral to weakly alkaline hot spring soil samples, soil, mud and a hot spring water containing microbial mats were collected from 5 points (metagenomic DNA samples N2, AR19, AR15, OJ1 and H1) at 3 locations in Japan where high temperature hot springs were spouting in the field. The temperature was in a range from 58 to 78° C. and the pH was in a range from 7.2 to 8 at the time of collection of these hot spring soil samples.

DNA was extracted from 10 g of each of the collected hot spring soil samples using a DNA extraction kit (ISOIL Large for Beads ver.2 manufactured by NIPPON GENE Co., Ltd.). For the genomic samples from which 10 μg or more DNA was obtained, 5 μg thereof was used to carry out the metagenomic sequencing. That is, with respect to the extracted DNA, using the GS FLX Titanium 454 manufactured by Roche Diagnostics K.K., the shotgun sequencing of metagenomic DNA and 16S rDNA amplicon was carried out. The rest of the DNA was used for the PCR cloning of cellulase gene. On the other hand, with the samples in which the amount of DNA was low (10 μg or less), genomes were amplified using a genomic DNA amplification kit (GenomniPhi V2 DNA Amplification Kit manufactured by GE Healthcare Inc.), and, for the resulting amplified products, sequencing of the metagenomic DNA was conducted.

The sequencing of metagenomic DNA was carried out 3 to 4 times for each hot spring soil sample and 19 times in total, to obtain a data set of whole genome sequence (WGS) with an average read length of 394 bp, the total read number of 26,295,463 and the total genome sequencing amount of 10.3 Gbp.

<2> Assemble and Statistics of Hot Spring Metagenomic Data

The output (sff files) of the Roche 454 was once again base called by PyroBayes (Quinlan et al. Nature Methods, 2008, vol. 5, p. 179-81.) to obtain sequence files in FASTA format and Quality value files. The resulting sequence reads were cut off at the ends to improve the quality and were assembled using assemble software Newbler version 2.3 or 2.5.3 provided by 454 Life Sciences.

The assembly was carried out under the settings of "minimum acceptable overlap match (mi)=0.9" and "option:—large (for large or complex genomes, speeds up assembly, but reduces accuracy.)".

A total of 2.5 Gbp of reads and assembled contigs of at least 100 bp that were processed with Quality filters were obtained, and this data set was used for the analysis of cellulase enzyme genes. Among the total read number of 26,294,193 reads, 17,991,567 leads were assembled into contigs of at least 1 kb on average (595.602 contigs in total), of which the maximum contig length was 278, 185 bp.

The sequences after assembly were referred to KEGG database (Kanehisa, M. Science & Technology Japan, 1996, No. 59, p. 34-38, http://www.genome.jp/kegg/,2011/5/11 (search)), and all contigs and singletons were classified into five categories of bacteria, archaea (archaebacteria), eukaryotes, viruses and those that do not belong to any of these categories. Among the sequence length (=total contig length+total singleton length) of 2.5 Gbp after assembly, the length of sequence that hit bacteria was 258 Mbp, the length of sequence that hit archaea was 27 Mbp, the length of sequence that hit eukaryotes was 193,561 bp (0.008% of the total sequence length after assembly), and the length of sequence that hit viruses was 685,640 bp (0.027% of the total sequence length after assembly). It was considered that the reason why only a small fraction of sequence belonged to eukaryotes was because it reflects the fact that the temperature of hot spring soil metagenome was in the range of 58 to 70° C. which was beyond the survival limit temperature of eukaryotic organisms such as filamentous fungi. From these results, it was found that this metagenome database only contained a mere 11.3% of the known DNA sequences. The length of sequence that did not belong to any categories was 2.2 Gbp and accounted for 88.7% of the entire sequence after assembly. These are novel sequences derived from any one of bacteria, archaea and eukaryotes.

<3> Prediction of Open Reading Frame (ORF) of Cellobiohydrolase

The sequences having EC numbers of 3.2.1.4 (cellulase), 3.2.1.37 (β-xylosidase), 3.2.1.91 (cellulose 1,4-β-cellobiosidase) and 3.2.1.8 (endo-1.4-β-xylanase) were download (access date: 2009 Apr. 13) from UniProt database (http://www.uniprot.org/), and a proteome local database for these glycoside hydrolase genes was established. Annotation software Orphelia (Hoff et al, Nucleic Acids Research, 2009, 37 (Web Server issue: W101-W105) was used for metagenomes AR15 and AR19, and Metagene (Noguchi et al, DNA Research, 2008, 15 (6)) was used for metagenomes H1, N2 and OJ1 to predict a gene region (=open reading frame) from the contig sequences obtained in the above section <2> (Orphelia option: default (model=Net700, max-overlap=60), Metagene option: -m). In order to extract the glycoside hydrolase genes, the estimated ORFs were referred to a local database using the BLASTP (blastall ver 2.2.18). Optional conditions of BLASTP were set to "Filter query sequence=false" and "Expectation value (E)<1 $e^{-20}$" [hereinafter, default value: Cost to open a gap=-1. Cost to extended gap=-1, X dropoff value for gapped alignment=0, Threshold for extending hits=0, and the Word size=default], and the hit sequences were collected as glycoside hydrolase genes.

Since the annotation software Orphelia and Metagene did not deal with a frame shift caused by the reading errors and the like, the frame shift correction was carried out in the manner described below. First, contigs were cut into a length of 2 kbp while shifting by 1 kbp. Therefore, the cut sequences overlapped with the upstream and downstream sequences by 1 kbp. Each of the cut contig sequences was searched against the proteome local database of the glycoside hydrolase genes described above (E<1 $e^{-20}$) and was screened by Blastx. A coding region for a glycoside hydrolase was acquired using Genewise (Wise2 package: http://www.ebi.ac.uk/Tools/Wise2/) against the hit contig sequences. At this time, sequences having the coding regions of 100 bp or smaller were removed. In the Genewise software, the target contig is referred to the hit enzyme sequence on the local database, and the frameshifts of sequences are corrected by inserting or deleting blanks (gaps) so as to maximize the alignment score.

The thus obtained glycoside hydrolases such as cellulases, endohemicellulases and debranching enzymes were subjected to functional classification on the basis of protein functional domain sequence database pfam HMMs (Pfam version 23.0 and HMMER v2.3; Finn et al, Nucleic Acids Research Database, 2010, Issue 38, p.D211-222). More specifically, the sequence homology search algorithm HMMER (Durbin et al., 'The theory behind profile HMMs. Biological sequence analysis: probabilistic models of proteins and nucleic acids', 1998, Cambridge University Press.; hmmpfam (Ver.2.3.2), E-value cutoff <1 $e^{-5}$; Database=Pfam_fs (models that can be used to find fragments of the represented domains in a sequence.)) applying a hidden Markov model was used to determine the glycoside hydrolase (GH) family from the homology search against the Pfam domain database. Screening by BLASTP was carried out, the 44 hit ORFs as CBH (cellobiohydrolase) sequences were classified into GH families.

<4> Corrections of Rare Initiation Codon Found in the Orphelia Output

The annotation software Orphelia detects ORFs using rare codons GTG (valine), TTG (leucine) and ATA (isoleucine) as the start codons, in addition to ATG (methionine). For this reason, when the assembled contigs did not include a full-length ORF that uses ATG as a start codon, Orphelia generates errors by recognizing rare codons as start codons. Among the full-length ORFs outputted by Orphelia in the above section <3>, 8 ORFs had rare codons GTG, TTG and ATA as initiation codons. By referring to the ORF output by Genewise and the amino acid sequence of the contig containing the ORFs, whether these ORFs are full-length sequences having rare codons as the start codons or output errors was confirmed. As a result, all the 8 ORFs outputted by Orphelia and having rare codons as the start codons were found to be output errors, i.e., incomplete length sequences.

TABLE 1

| Metagenome | GH family classification of cellobiohydrolase genes | | | | | |
|---|---|---|---|---|---|---|
|  | GH6 | GH7 | GH9 | GH48 | Other GHs | Total |
| AR19 | 2 (0) | 0 | 2 (2) | 5 (1) | 4 (3) | 13 (6) |
| AR15 | 0 | 0 | 1 (1) | 2 (1) | 3 (2) | 6 (4) |
| OJ1 | 2 (0) | 0 | 7 (2) | 2 (1) | 4 (2) | 15 (5) |
| N2 | 0 | 0 | 5 (3) | 3 (0) | 2 (2) | 10 (5) |
| H1 | 0 | 0 | 0 | 0 | 0 | 0 |
| Total number of ORFs | 4 (0) | 0 (0) | 15 (8) | 12 (3) | 13 (9) | 44 (20) |

The results of classification of the 44 ORFs that were predicted as cellobiohydrolase genes into GH families are shown in Table 1. In Table 1, the number of full-length ORFs having methionine as the start codon is indicated in parentheses. As shown in Table 1, a total of 4 cellobiohydrolase ORFs (2 from the metagenome AR19 (AR19G-166 and AR19G-12) and 2 from the metagenome OJ1 (OJ1-1 and OJ1-2)) belonging to GH6 family were obtained. On the other hand, ORF sequences belonging to GH7 family were not obtained. 15 ORFs belonging to GH9 family and 12 ORFs belonging to GH48 family were obtained, respectively. A total of 13 cellobiohydrolase gene ORFs belonging to other GH families (GH10. GH12, and GH26) was obtained. For all of these ORFs predicted to be cellobiohydrolase genes including the incomplete length sequences, primers were designed and the genes were cloned from the hot spring soil metagenomic DNA by PCR.

It should be noted that the cellulase enzyme solutions for biofuels that have been put into practical use at present are Novozyme CELLIC (registered trademark) CTec2 (http://www.bioenergy.novozymes.com/cellulosic-ethanol/) and Genencor Accellerase (registered trademark) TRIO (http://www.genencor.com/industries/biofuels/fuel_ethanol_from_biomass_cellulosic_biofuels/), and both are based on an enzyme secreted by a wood rotting fungus *Trichoderma reesei*. Major constitutive enzymes of the glycoside hydrolase (GH) secreted by this filamentous fungus are cellobiohydrolases CBHI and CBHII, which belong to GH17 family and GH116 family, respectively.

<5> Open Reading Frames OJ1-1 and OJ1-2

An open reading frame OJ1-1 was found to encode a multi-domain enzyme constituted of 548 amino acid residues and having a cellulose binding module CBM3 (149 bp), a linker (111 bp) and a GH6 catalytic domain. However, the second half of the catalytic domain was lacking a stop codon and of incomplete length.

An open reading frame OJ1-2 was a nucleotide sequence encoding a polypeptide constituted of 247 amino acid residues and composed of only GH6 catalytic domain. OJ1-2 is an incomplete sequence because OJ1-2 lacks both an initiation codon and a stop codon, and cellobiohydrolases of GH6 family are usually composed of 400 or more amino acid residues. The amino acid sequence of OJ1-2 is a sequence 100% identical to the amino acid sequence of the open reading frame AR19G-12, and from this result, it is thought that OJ1-2 is the same gene as AR19G-12 and is a partial sequence of AR19G-12.

<6> Open Reading Frames AR19G-166 and AR19G-12

An open reading frame AR19G-166 was encoding a polypeptide (SEQ ID NO: 5) composed of 474 amino acid residues, although it was a sequence of incomplete length missing an initiation codon and was composed of only a partial sequence of a linker and a GH6 catalytic domain. The GH6 catalytic domain (AR19G-166RA, SEQ ID NO: 6) of AR19G-166 exhibited 66% amino acid sequence identity with a glycoside hydrolase (Genbank: ABX04776.1) of a *Chloroflexi* mesophilic aerobic bacterium *Herpetosiphon aurantiacus* DSM 785.

An open reading frame AR19G-12 was encoding a polypeptide (SEQ ID NO: 7) composed of 459 amino acid residues, although, just like the open reading frame AR19G-166, it was a sequence of incomplete length missing an initiation codon and was composed of a partial sequence of a linker and a GH6 catalytic domain. The GH16 catalytic domain (AR19G-12L1, SEQ ID NO: 1) of AR19G-12 exhibited 63% amino acid sequence identity with a CBH catalytic domain of GH6 (Family 6 glycoside hydrolase) (NCBI Reference Sequence-YP_001544904.1) of *Herpetosiphon aurantiacus* DSM 785.

Figure 1:
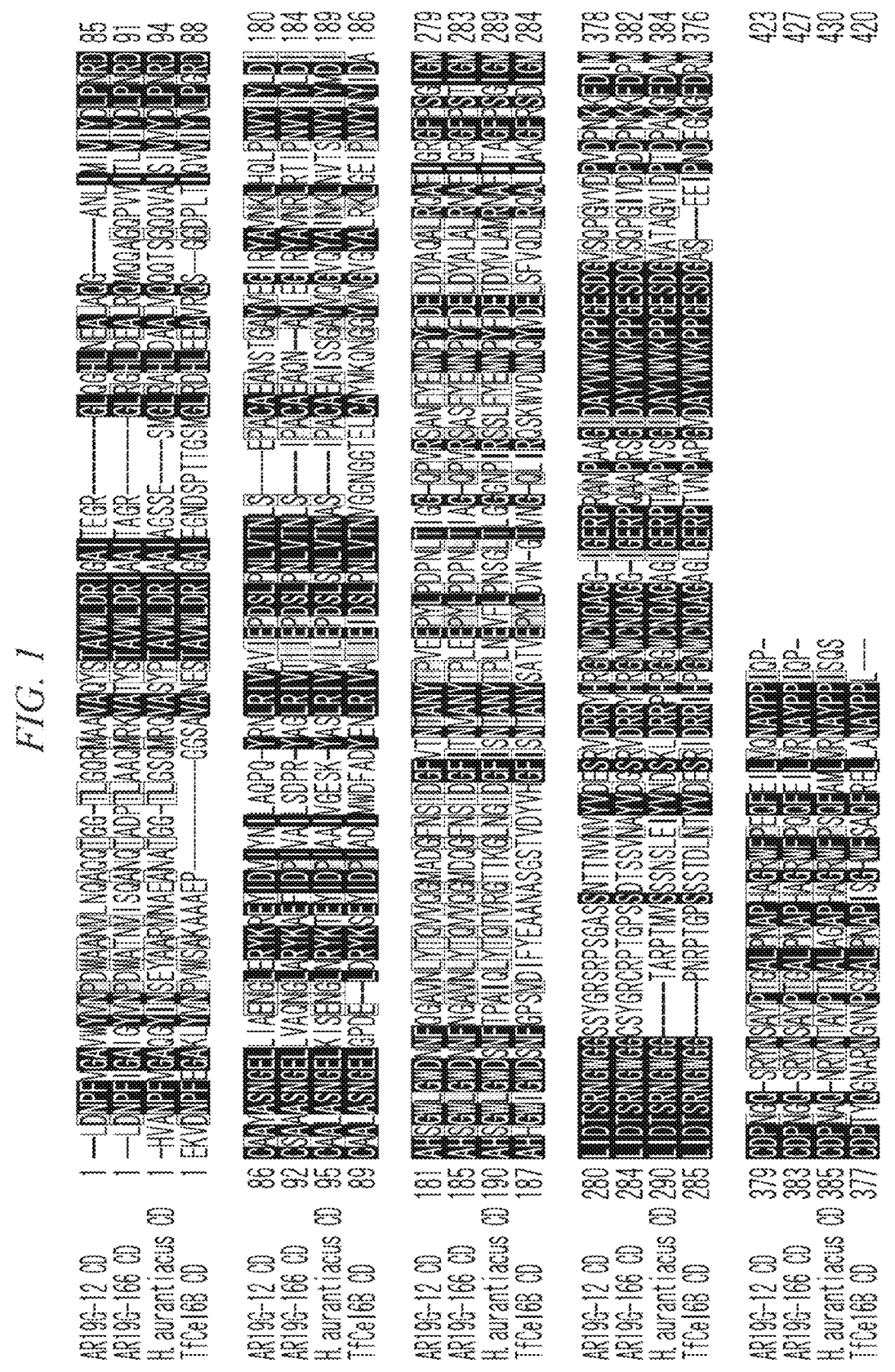

FIG. 1 shows an amino acid sequence alignment of catalytic domains of the open reading frames AR19G-166 and AR19G-12, a GH6 cellobiohydrolase catalytic domain (SEQ ID NO: 8) of a mesophilic aerobic bacterium *Herpetosiphon aurantiacus* belonging to the phylum *Chloroflexi* and a catalytic domain (SEQ ID NO: 9) of a GH16 cellobiohydrolase TfCel6B (GenBank: AAA62211.1) of a thermophilic soil actinomycete *Thermobifida fusca*. In FIG. 1, amino acids shown in black, rather than in white, indicate a region where amino acid residues are conserved in all of these amino acid sequences, and shaded amino acids indicate, although some mutations are present among these amino acid sequences, a region where the amino acid residues are conserved in majority of these amino acid sequences.

<Systematic Genetic Analysis>

Unlike the genes cloned from cultured and isolated cells, origins of genes cloned by metagenome analysis are unknown. It is unclear whether the 4 open reading frames AR19G-166, AR19G-12 (OJ1-2) and OJ1-1 that were obtained from the high temperature soil metagenome and belonged to GH16 family were derived from prokaryotes, such as bacteria and archaea (archaebacteria), or derived from eukaryotes, such as filamentous fungi and mushrooms. Therefore, a systematic genetic analysis was carried out by a multiple alignment and molecular phylogenetic tree of amino acid sequences of the catalytic domains to predict the origins of these ORFs.

FIG. 2 is a rooted molecular phylogenetic tree of exo-type glycoside hydrolases (cellobiohydrolases, glycoside hydrolases, exoglucanases and cellobiosidases) belonging to GH6 family. With respect to the amino acid sequences deduced from the open reading frames AR190-166, AR190-12 (OJ1-2) and OJ1-1 and an amino acid sequence of a catalytic domain of Cel6B (GenBank: AAA62211.1) of a thermophilic actinomycete *Thermobifida fusca* YX having a cellulose degrading capability, a homology search against Genbank by BLASTP was carried out to obtain sequences of 35 types of glycoside hydrolases belonging to family 6. These 35 hits of bacterial sequences by the homology search and the amino acid sequences deduced from the open reading frames AR19G-166, AR19G-12 (OJ1-2) and OJ1-1 were used for a multiple alignment (Cost Matrix=Blosum80; Gap open penalty=12; Gap extension penalty=3; Alignment type=Global alignment with free end gaps) using Geneious Pro 5.6.5, and then a phylogenetic tree was created by a neighbor joining method. An endoglucanase Cel6A (Genbank: AAC06388.1) of *Thermobifida fusca* YX belonging to GH6 family was used as an outgroup. Bootstrap values were calculated from 1.000 replicates and shown in percentage at each branch point of the phylogenetic tree. In FIG. 2, the scale shown at the bottom indicates a genetic distance (average number of amino acid substitutions/site). In addition, enzyme names "CBH" and "GH" shown in parentheses are abbreviations of cellobiohydrolase or 1,4-beta-cellobiohydrolase and glycoside hydrolase, respectively.

The family 6 glycoside hydrolases of bacteria and filamentous fungi that were used for the reference of the phylogenetic tree were as follows (those indicated in parentheses are the accession numbers in Genbank, Protein Data bank (PDB) or EMBL-Bank).

*Acidothermus cellulolyticus* 11B glycoside hydrolase, family 6 (Genbank: ABK52388.1);

*Amycolatopsis mediterranei* U32 1,4-beta-cellobiosidase (Genbank: ADJ46954.1);

*Cellulomonas fimi* ATCC 484 1,4-beta-cellobiohydrolase (Genbank: AEE46055.1);

*Cellulosimicrobium* sp. HY-13 exo-beta-1,4-xylanase (Genbank: ADR71224.1);

*Cellvibrio japonicus* Ueda 107 Cellobiohydrolase, putative, cel6A (Genbank: ACE85978.1);

*Hahella chejuensis* KCTC 2396 Cellobiohydrolase A (Genbank: ABC27007.1);

*Herpetosiphon aurantiacus* DSM 785 glycoside hydrolase family 6 (Genbank: ABX04776.1);

*Jonesia denitrificans* DSM 20603 glycoside hydrolase family 6 (Genbank: ACV08399.1);

*Kitasatospora setae* KM-6054 putative glucanase (Genbank: BAJ26185.1);

*Ktedonobacter racemifer* DSM 44963 1,4-beta-cellobiohydrolase (Genbank: EFH85864.1);

*Leptolyngbya* sp. PCC 7375 1,4-beta-cellobiosidase A (NCBI Reference Sequence: WP_006518953.1);

*Micromonospora aurentiaca* ATCC 27029 1,4-beta-cellobiohydrolase (Genbank: ADL48574.1);

*Micromonospora lupini* str. Lupac 08 1,4-beta-cellobiohydrolase (Genbank: CCH20969.1);

*Nocardiopsis dassonvillei* subsp. dassonville DSM 431111, 1,4-beta-cellobiohydrolase (Genbank: ADH67869.1);

*Paenibacillus curdlanolyticus* Y K9 1,4-beta-cellobiohydrolase (Genbank: EFM08880.1);

*Paenibacillus mucilaginosus* 3016 exoglucanase A (Genbank: AFC32454.1):

*Ralstonia solanacearum* Po82 CbhA (Genbank: AEG71050.1);

*Saccharophagus degradans* 2-40 putative cellobiohydrolase (Genbank: ABD81532.1);

*Salinispora arenicola* CNS-205 glycoside hydrolase family 6 (Genbank: ABV99773.1);

*Shewanella violacea* DSS 12 1,4-beta-cellobiosidase (NCBI Reference Sequence. YP_003555620.1);

*Stackebrandtia nassauensis* DSM 44728 1,4-beta-cellobiosidase (Genbank: ADD42622.1);

*Stigmatella aurantiaca* DW4/3-1 exoglucanase A (Genbank: EAU67050.1);

*Streplomyces avermitilis* MA-4680 1,4-beta-cellobiosidase (Genhank: BAC69564.1);

*Sreplomyces griseoaurantiacus* 1,4-beta-cellobiosidase (NCBI Reference Sequence: WP_006142911.1);

*Streptosporangium roseum* DSM 43021 cellobiohydrolase A (NCBI Reference Sequence: YP 003342336.1);

*Teredinibacter turnerae* T7901 cellobiohydrolase (Genbank: ACR 12723.1);

*Thermobifida fisca* YX cellobiohydrolase Cel6B (Genbank: AAA62211.1);

*Thermobispora bispora* DSM 43833 family 6 glycoside hydrolase (NCBI Reference Sequence: YP_003653250.1):

uncultured organism putative cel6A cellobiohydrolase (GenBank: ACY24855.1);

*Verrucosispora maris* AB-18-032 1,4-beta-cellobiohydrolase (Genbank: AEB46944.1);

*Xanthomonas campestris* pv. *raphani* 756C exoglucanase A (Genbank: AEL08359.1);

*Xanthomonas oryzae* pv. *orzyae* KACC 10331 1,4-beta-cellobiosidase A (Genbank: AAW77289.1):

*Xanthomonas vesicatoria* ATCC 35937 1,4-beta-cellobiosidase (NCBI Reference Sequence: WP 005993732.1);

*Xylanimonas cellulosilytica* DSM 15894 glycoside hydrolase family 6 (Genbank: ACZ30181.1);

*Xylella fastidiosa* EB92.1 cellobiohydrolase A (Genbank: EGO81204.1).

As shown in FIG. 2, it was found that the 4 open reading frames AR19G-166, AR19G-12 (OJ1-2) and OJ1-1 belonging to GH6 family obtained by metagenomic analysis was forming the same clade with a glycoside hydrolase (GenBank: ABX04776.1) of mesophilic aerobic bacterium *Herpelosiphon aurantiacus* DSM 785 belonging to the phylum *Chloroflexi*.

A catalytic domain (AR19G-12L1) of the open reading frame AR19G-12 exhibited an amino acid sequence identity of 79% with a catalytic domain (AR19G-166RA) of AR19G-166 whose cellobiohydrolase activity was verified, and exhibited an amino acid sequence homology of 63% with the GH6 cellobiohydrolase CBH of *Herpetosiphon aurantiacus* DSM 785 in the same clade, which indicated a novel protein. On the other hand, the catalytic domain of AR19G-12 only exhibited an amino acid sequence homology of 53% with the catalytic domain of TfCel6B of thermophilic soil actinomycete *Thermobifida fusca* on which the most detailed analysis and characterization such as enzyme activity, optimum temperature, optimum pH, cellobiose inhibition and X-ray three-dimensional structure have been performed, among the bacterial cellobiohydrolases belonging to GH6 family.

Figure 3:
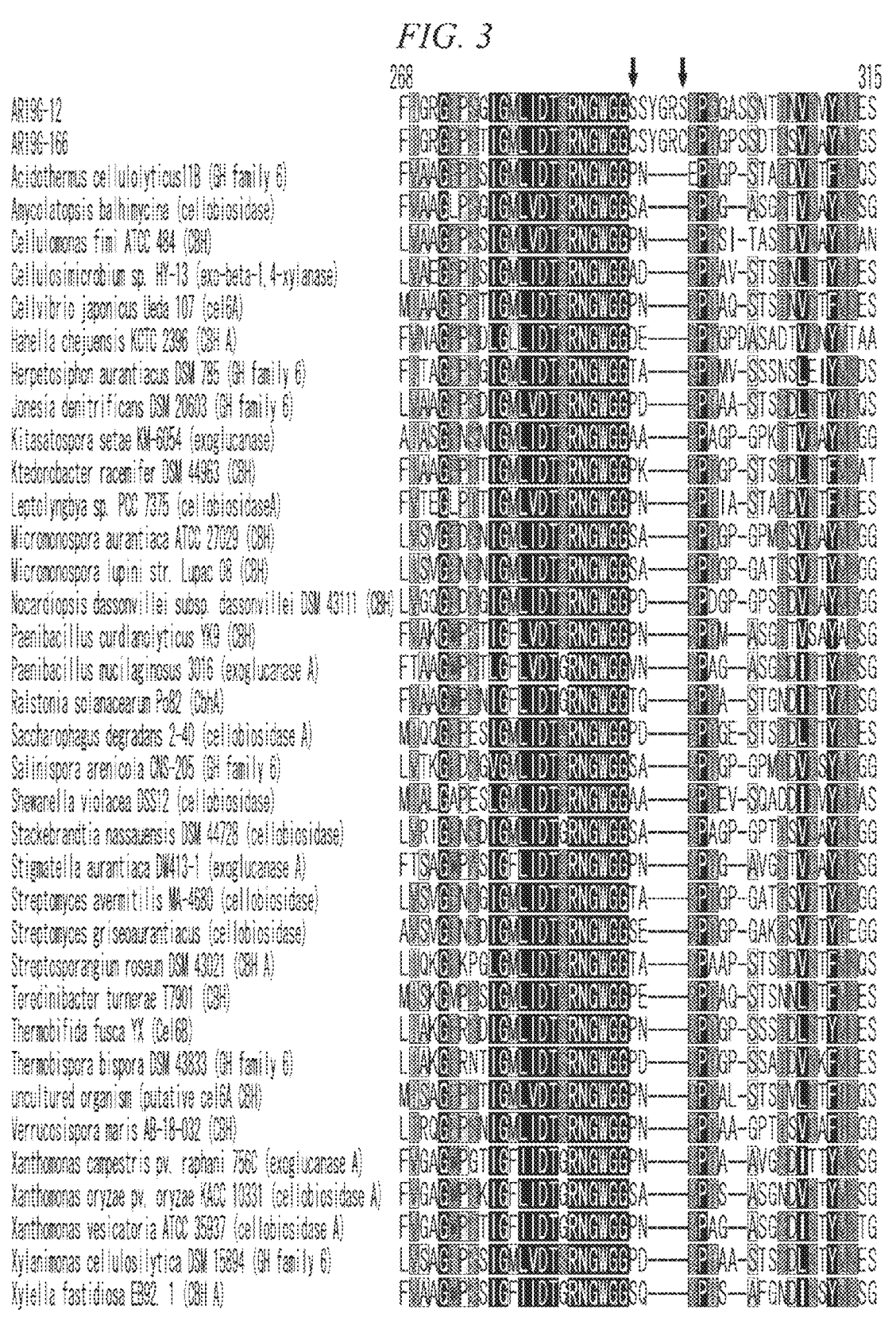

From the sequence alignment of the open reading frame AR19G-12, the open reading frame AR19G-166, and the catalytic domains of 34 types of bacterial GH6 CBH, it was found that one site where 4 amino acid residues are inserted was present in the two ORFs, which was not present in other bacterial CBH belonging to GH6 family. A sequence alignment of a sequence of amino acid residues from the position 268 to the position 315 among the catalytic domain (AR19G-12L1) of a protein encoded by AR19G-12, AR19G-166RA (CBH domain of a protein encoded by the open reading frame AR19G-166) which was homologous (sequence identity) to this sequence, and amino acid residues of catalytic domains of 34 types of bacterial GH6 CBH is shown in FIG. 3. The enzyme names deduced from sequence homology were indicated in parentheses after the species names other than *Thermobifida fusca*, and glycoside hydrolases and cellobiohydrolases are abbreviated as GH and CBH, respectively.

<7> Gene Cloning

The catalytic domains of the cellobiohydrolase candidate genes AR19G-12 and AR19G-166 obtained by shotgun sequencing and assembly of metagenomic DNA were amplified by PCR using the hot spring soil DNA amplified by a genomic DNA amplification kit (GenomiPhi V2 DNA Amplification Kit, manufactured by GE Healthcare) as a template. The amplified PCR product was inserted into a pET101/D-TOPO vector of Champion pET Directional TOPO (registered trademark) Expression Kits (manufactured by Life Technologies Inc.) and transformed into a One Shot TOP10 strain. Positive clones were selected by colony PCR and were cultured for 17 to 20 hours at 37° C. and 200 rpm using an LB liquid medium containing 100 mg/L of ampicillin, and then plasmids were prepared using a miniprep kit (Wizard (registered trademark) plus SV Minipreps DNA Purification System, manufactured by Promega). Sequence confirmation was carried out for the prepared plasmids using a 3730 DNA Analyzer sequencer manufactured by Life Technologies.

<8> Preparation of Amino Acid Substituted Variants S291C/S296C

As shown in FIG. 3, by an amino acid sequence alignment of the catalytic domains of bacterial GH6 CBH, at the insertion site of the 4 amino acid residues that was present only in AR19G-12L1 and AR19G-166RA, the two genes were different by the amino acid residues at two sites (amino acid residues at positions 291 and 296 in AR19G-12L1). Both cysteine residues of AR19G-166RA had been replaced by serine in AR19G-12L1. Then, amino acid substituted variants S291C/S296C of AR19G-12L1 in which the serine was replaced by cysteine were produced by a QuickChange Site-Directed Mutagenesis Kit (manufactured by Agilent Technologies, Inc.).

<9> Gene Expression and Purification of Cellobiohydrolase Enzyme Protein

After sequence confirmation, the plasmid with the gene of interest was introduced into *E. coli* cells for the protein expression by a heat shock method. A BL21 Star (DE3) strain that comes with the Champion pET Directional TOPO (registered trademark) Expression Kits (manufactured by Life Technologies, Inc.) or a Rosetta-gamiB (DE3) pLysS strain (manufactured by Merck) was used as competent cells for transformation. *E. coli* cells with the gene of interest were inoculated into the LB medium and incubated to an OD600 of about 0.2 to 0.8, and after adding IPTG (Isopropyl-βD(−)-thiogalactopyranoside) thereto, cultured further for 5 to 20 hours, thereby inducing the expression of the target protein.

By this operation, the AR19G-166RA gene was expressed satisfactorily. However, for the catalytic domain of AR19G-12 (AR19G-12L1 gene), in spite of encoding a relatively similar amino acid sequence (79% amino acid sequence identity) to that of AR19G-166RA, the expression of an enzyme protein encoded by this gene was not achieved.

The GC content of the catalytic domain of the cloned AR19G-12L1 gene was 63.6%, whereas the GC content of the catalytic domain of the AR19G-166RA gene was 57.2%. The AR19G-12L1 gene had a higher GC content than the AR19G-166RA gene by 6.4%, and it was considered that this high GC content was possibly inhibiting the expression of the enzyme protein. Therefore, the AR19G-12L1 gene was integrated into an Expression Vector pLEAD (manufactured by NIPPON GENE Co., Ltd.) to transform a JM109 strain. The expression vector pLEAD is a vector that has been developed by the expression efficiency screening of genes of high GC content and has been shown to be effective for the expression of genes of high GC content which is difficult to express in a conventional E. coli expression vector (Suzuki et al., J. Biochem., 1997, vol. 121, p. 1031-1034; Ishida and Oshima, J. Biochem., 2002, vol. 132, p. 63-70). As a result, expression of the enzyme protein encoded by the AR19G-12L1 gene was confirmed.

More specifically, the E. coli clones retaining the plasmid with the AR19G-121.1 gene and the E. coli clones retaining the plasmid with a gene (S291C/S296C gene) of amino acid substituted variants S291C/S296C of the AR19G-12L1 gene were each inoculated into 5 mL of an LB medium containing 100 mg/L of ampicillin and cultured with shaking for 20 hours at 37° C. After culturing, the E. coli cells were collected by centrifugation and suspended by the addition of 50 mM Tris-HCl Buffer (pH 8.0) of 1/10 volume of the culture medium. Then, a process of disrupting for 30 seconds with a sonication apparatus BioRuptorUCD-200T (manufactured by Cosmo Bio Inc.), followed by pausing for 30 seconds was carried out 10 times to obtain a supernatant after centrifugation (E. coli crude extract). A portion of the above E. coli crude extract was electrophoresed by SDS-PAGE to confirm the expression of the target protein of an expected size. After the confirmation of protein expression, and the solution of B. coli incubated overnight at 37° C. was used as a preculture for the main culture in 100-fold volume of an LB medium containing 100 mg/L ampicillin. The E. coli crude extract obtained by sonication in the same manner as described above was filtered using a filter (pore size φ=0.45 μm, manufactured by Millipore Inc.), and the resulting filtrate was used as a crude enzyme sample solution.

The crude enzyme sample solution was loaded onto an ion exchange column HiTrap Q HP (manufactured by GE Healthcare) equilibrated with 50 mM Tris-HCl buffer (pH 8.0), and a medium-high pressure liquid chromatography system AKTA design (manufactured by GE Healthcare) was used to fractionate proteins with a concentration gradient of 0 to 50% in 50 mM Tris-HCl buffer (pH 8.0) containing 1M of NaCl. Fractions with a cellobiohydrolase activity were pooled, and the buffer was exchanged to a 50 mM Tris-HCl buffer (pH 8.0) containing 750 mM of ammonium sulfate using a centrifugal ultrafiltration membrane VIVASPIN 20 (manufactured by Sartorius stedim). The sample was loaded onto a hydrophobic interaction separation column HiTrap Phnenyl HP (manufactured by GE Healthcare) equilibrated with the same solution, and proteins were eluted with a concentration gradient of 0 to 100% in 50 mM Tris-HCl buffer (pH 8.0). Fractions with a cellobiohydrolase activity were pooled and then concentrated using the VIVASPIN 20 until the liquid volume reached about 8 mL. The concentrated sample was loaded onto a gel filtration column Hiload 26/60 superdex 200 μg (manufactured by GE Healthcare) equilibrated with 50 mM Tris-HCl buffer (pH 8.0) containing 150 mM of NaCl, and was fractionated by flowing the same buffer of 1 to 1.5 volume of the column volume at a flow rate of 2 to 3 mL/min. Fractions with a cellobiohydrolase activity were pooled and concentrated, and the buffer was exchanged to a 50 mM Tris-HCl buffer (pH 8.0) to obtain a purified enzyme sample solution at a final concentration of about 1 mg/mL.

Figure 4:
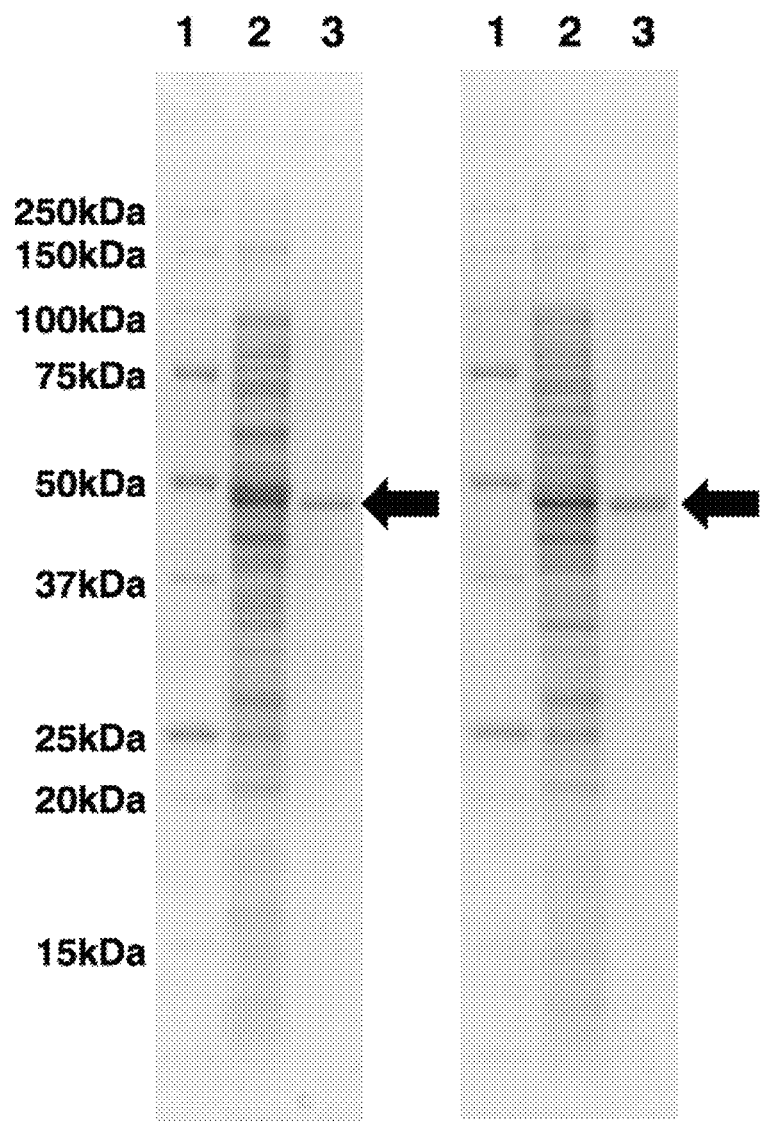
FIG. 4 is a diagram showing the result of an SDS-PAGE analysis of AR19G-12L1 protein and its amino acid substituted variants S291C/S296C proteins that are expressed in *Escherichia coli* in Example 1.

The crude enzyme sample solution and the purified enzyme sample solution were confirmed by SS-PAGE analysis. The results of SDS-PAGE analysis of the crude enzyme sample solution and the purified enzyme sample solution of the transformed E. coli cells into which the AR19G-12L1 gene and the amino acid substituted variants S291C/S296C gene had been introduced are shown in FIG. 4. It is an electrophoretic pattern in which a protein molecular weight marker was run in lane 1, the crude enzyme sample solution was run in lane 2 and the purified enzyme sample solution was run in lane 3. As a result, in both cases when the AR19G-12L1 gene was introduced ("AR19G-12" in the figure) and when the S291C/S296C gene was introduced ("S291C/S296C" in the figure), a strong band was observed near a molecular weight of 46.5 kDa expected from the amino acid sequence (SEQ ID NO: 1 and 3) in the crude enzyme sample solution, and a single band corresponding to the above band was observed in the purified enzyme sample solution (indicated by arrows in the figure).

Cellobiohydrolase genes are, in general, very poorly expressed. For example, in the case of expressing a cellobiohydrolase gene using E. coli as a host, the gene is hardly expressed regardless of whether it is derived from filamentous fungi or derived from bacteria. On the other hand, by simply using an expression vector effective for the expression of genes of high GC content, it was possible to satisfactorily express both the AR19G12L1 gene and the S291C/S296C gene in E. coli strain JM109 for transformation.

<10> Measurement of Cellobiohydrolase Activity (PSA Hydrolytic Activity)

Phosphoric acid swollen Avicel (PSA) was used as a substrate for the cellobiohydrolase activity measurement of the enzyme.

The PSA was prepared by first dissolving an Avicel powder (microcrystalline cellulose powder manufactured by Merck) with a phosphoric acid solution, followed by the addition of purified water thereto for precipitation, and then washing until a pH of 5 or more was reached. It should be noted that all the PSA used in the subsequent experiments was prepared by the aforementioned method.

The PSA activity measurement of the purified enzyme sample solution (final concentration: about 1 mg/mL) prepared in the above section <9> was carried out by reacting a mixed solution composed of 50 μL of 200 mM acetate buffer (pH 5.5), 40 μL of purified water and 10 μL of the purified enzyme with 100 μL of an aqueous solution containing 1% by mass of PSA for 20 minutes at 30 to 99° C.

In all measurements, a mixed solution prepared by a reaction under the same conditions by adding 50 mM Tris-HCl buffer (pH 8.0) in place of the purified enzyme sample solution was used as a control. In addition, the purified enzyme mixture and the above mixture as a control were kept for 5 minutes at the reaction temperature and then mixed with a substrate solution which was kept in the same manner to initiate the reaction. During reaction, in order to prevent the precipitation of insoluble substrates, all the mixtures were stirred using an Eppendorf Thermomixer (1,400 rpm). After the completion of the reaction, an equal volume of 3,5-dinitrosalicylic acid reagent (DNS solution) was added thereto, and the resulting mixture was subjected to a heat treatment for 5 minutes at 100° C. and was centrifuged after 5 minutes of cooling to obtain a supernatant. The absorbance at 540 nm was measured using a spectrophotometer, and the amount of reduced sugar in the supernatant was calculated using a calibration curve prepared with glucose to determine the amount of reduced sugar produced by the hydrolysis of the enzyme from the difference with the control. The enzyme activity for producing 1 μmol of a reduced sugar per minute was defined as 1 U, and the value obtained by division by the amount of protein was defined as a specific activity (U/mg).

<11> Substrate Specificity of Cellobiohydrolase

From the homology of amino acid sequence, the AR19G-12 gene is thought to be a cellobiohydrolase belonging to GH6 family. Therefore, by using the purified enzyme sample solution (final concentration: about 1 mg/mL), the hydrolytic activities against PSA, Avicel powder, CMC (carboxymethyl cellulose, manufactured by Sigma), xylan (derived from beechwood, manufactured by Sigma), lichenan (Lichenan, manufactured by MP Biomedicals Inc.) and laminarin (derived from Laminaria digitata, manufactured by Sigma) were measured, and the substrate specificity of the AR19G-12L1 protein and the amino acid substituted variant S291C/S296C protein was determined.

After preincubating a mixed solution composed of 50 μL of 200 mM acetate buffer (pH 5.5), 40 μL of purified water and 10 μL of the purified enzyme for 5 minutes at 50° C., 100 μL, of a 1% by mass aqueous solution of each substrate was further added thereto to allow the reaction to proceed for 20 minutes at 70° C. When the Avicel powder was used as a substrate, another experiment of 2 hours was carried out. After the hydrolysis reaction, the amount of reduced sugar produced by enzymatic hydrolysis was determined, and the specific activity (U/mg) was calculated. Each measurement was carried out by three independent trials and the average value and the standard errors were determined.

The measurement results of AR19G-121.1 and the measurement results of amino acid substituted variant S291C/S296C are shown in FIG. 5 and FIG. 6, respectively. As a result, AR19G-12L1 and amino acid substituted variant S291C/S296C exhibited a high hydrolytic activity against water-soluble PSA (2.01252 U/mg, 3.47781 U/mg). In addition, degradation activities against lichenan composed of β-1,3- and β-1.4 glucan and crystalline cellulose Avicel were also exhibited (0.31896 U/mg, 0.5874 U/mg). On the other hand, degradation activities against CMC, laminarin composed of β-1.3- and β-1,6 glucan, and xylan were hardly exhibited. The enzyme substrate specificity exhibiting a hydrolytic activity against crystalline cellulose Avicel in spite of being very weak (0.24712 U/mg, 0.2187 U/mg) while exhibiting no degradation activity against CMC and xylan indicates that AR19G-12 is a cellobiohydrolase belonging to GH6 family.

<12> Temperature and pH Dependencies of Cellobiohydrolase Activity

The temperature dependency and pH dependency of the PSA hydrolytic activity by AR19G-12L1 and amino acid substituted variant S291C/S296C were examined. The purified enzyme sample solution (final concentration of about 1 mg/mL) obtained in the above section <9> was used for the measurement.

The measurement of temperature dependency of PSA hydrolytic activity of the purified enzyme was carried out in the same manner as in the above section <10> with the exception that a mixed solution composed of 100 μL of a 1% by mass PSA aqueous solution, 50 μL of acetate buffer (pH 5.5), 40 μL of purified water and 10 μL of the purified enzyme was allowed to react for 20 minutes at 30, 40, 50, 60, 65, 70, 75, 80, 85, 90 or 99° C. to determine the amount of reduced sugar produced by enzymatic hydrolysis and to calculate the PSA hydrolytic activity (U/mg).

The measurement of pH1 dependency of PSA hydrolytic activity of the purified enzyme was carried out in the same manner as in the above section <10> with the exception that a mixed solution composed of 100 μL of a 1% by mass PSA aqueous solution, 50 μL of Mellvaine buffer (pH 3 to 8), 40 μL of purified water and 10 μL of the purified enzyme was allowed to react for 20 minutes at 50° C. or 70° C. to determine the amount of reduced sugar produced by enzymatic hydrolysis and to calculate the PSA hydrolytic activity (U/mg).

Figure 7:
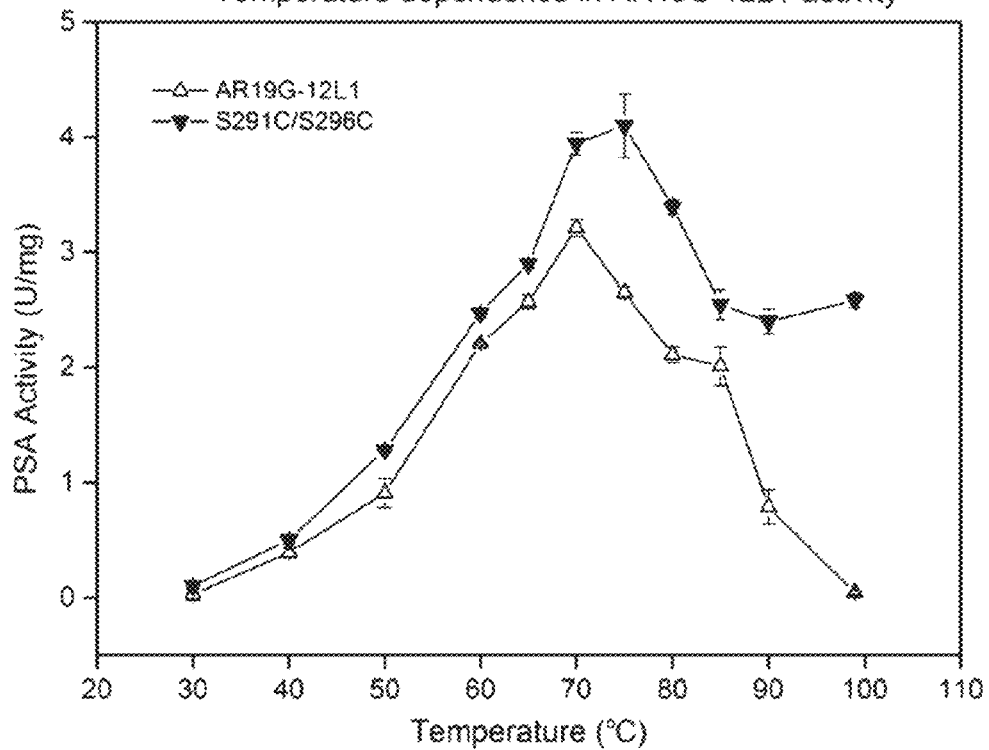
FIG. 7 is a diagram showing the measurement results of PSA hydrolytic activities at each temperature of AR19G-12L1 protein and its amino acid substituted variants S291C/S296C proteins that are expressed in *E. coli* in Example 1.
Figure 8:
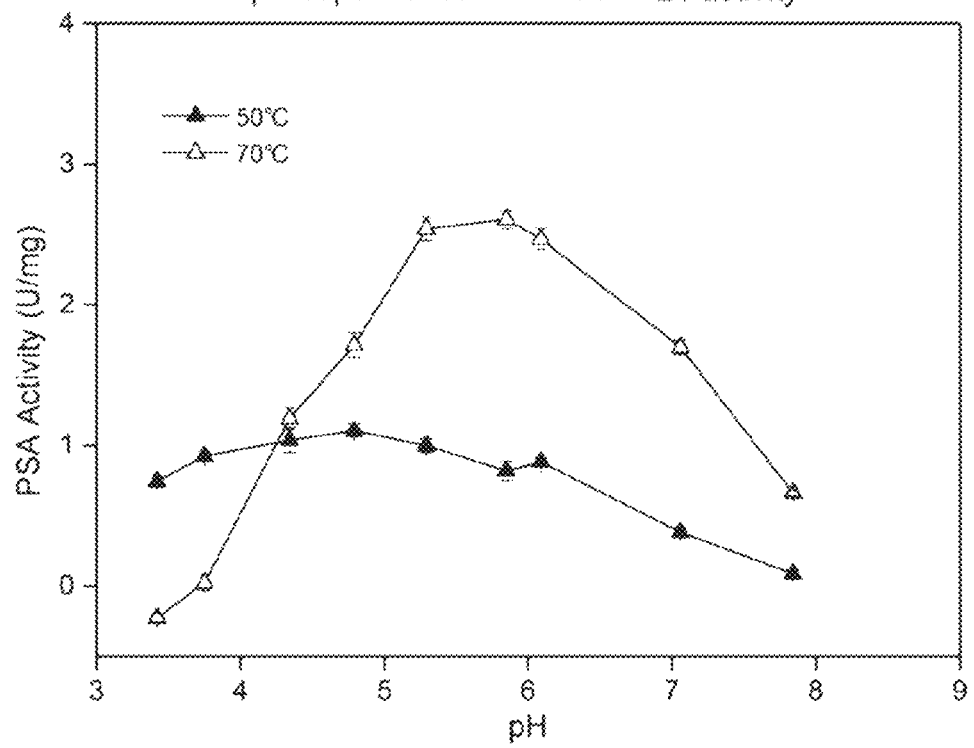
FIG. 8 is a diagram showing the measurement results of the PSA hydrolytic activity (at 50° C. or 70° C.) of the AR19G-12L1 protein expressed in *E. coli* in Example 1 at each pH.

The measurement results are shown in FIGS. 7 and 8. FIG. 7 is a diagram showing the results of measuring the PSA hydrolytic activities (pH 5.5) at each temperature by plotting the temperature on the horizontal axis, and FIG. 8 is a diagram showing the results of measuring the PSA hydrolytic activity at each pH at 50° C. or 70° C. of the purified enzyme AR19G-12L1 by plotting the pH on the horizontal axis. The measured pH values of a mixed solution of a substrate, buffer and enzyme were plotted.

The purified enzyme AR19G-12L1 exhibited a high PSA hydrolytic activity in a temperature range of 60 to 80° C. (FIG. 7, Δ).

The optimum temperature ($T_{opt}$) showing the highest activity was 70° C. at a pH of 5.5. When the enzyme reaction temperature was set to 90° C. or higher, the PSA hydrolytic activity of the purified enzyme AR19G-12L1 was rapidly reduced.

On the other hand, the purified enzyme amino acid substituted variant S291C/S296C had the optimum temperature ($T_{opt}$) that showed the highest activity of 75° C. at a pH of 5.5, which was higher than the optimum temperature of the wild type AR19G-12L1 (FIG. 7, ▼). The PSA hydrolytic activity of the purified enzyme S291C/S296C did not reduce even at the enzyme reaction temperature of 90 to 99° C., and the activity of 60% or higher at the time of the optimum temperature of 75° C. was maintained.

The purified enzyme AR19G-12L1 exhibited the highest PSA hydrolytic activity in the reaction temperature range of 65 to 80° C. and in the pH range of 4 to 6 (FIGS. 7 and 8). The optimum pH varies depending on the reaction temperature, and the optimum pH was 4.6 (measured value) at 60 to 65° C., the optimum pH was 5.2 to 5.3 (measured value) at 70 to 75° C., and the optimum pH1 was 5.8 (measured value) at 80° C. Low levels of PSA hydrolytic activity were observed in a pH range of 3.2 to 4.5 and in a pH range of 7 to 8. On the other hand, like the purified enzyme AR19G-12L1, the purified enzyme S291C/S296C showed the highest PSA hydrolytic activity in the pH range of 4 to 6, and low levels of PSA hydrolytic activity were observed in a pH range of 3.2 to 4.5 and in a pH range of 7 to 8 (FIGS. 7 and 8).

<13> Thermal Stability Measurement of Cellobiohydrolase by Differential Scanning Fluorimetry Differential scanning fluorimetry (DSF) is one of the methods of measuring the thermal denaturation of proteins using a fluorescent dye and real-time PCR machine, and can be applied to various proteins. The fluorescent dyes used in the DSF such as SYPRO Orange emit fluorescence in nonpolar conditions when binding to the hydrophobic site, while the emission is suppressed in the polar conditions when dissolved in water. Usually, the protein structure is unfolded in the thermal denaturation temperature, and the hydrophobic regions of the protein are exposed to the protein surface. When SYPRO Orange binds to this exposed hydrophobic region, by the excitation light having a wavelength of 470 to 480 nm, strong fluorescence having a peak near a wavelength of 595 nm is emitted. By increasing the temperature of the protein solution at regular intervals in a stepwise manner and measuring the fluorescence intensity, the thermal degradation temperature (=change point of the fluorescence intensity) is calculated.

More specifically, 2 μL of 100-fold diluted SYPRO Orange (manufactured by Life Technologies Inc.), 1 μL of the enzyme protein with a concentration of 1 mg/mL, 5 μL of 200 mM acetate buffer (pH 5.5) and 12 μL of purified water were added into the wells of a 96-well PCR plate (Multiplate 96 Well PCR Plate MLL-9651, manufactured by Bio-Rad Laboratories, Inc.) so that the volume of each well was 20 μL. The PCR plate was sealed with Optical Flat 8-Cap Strips (manufactured by Bio-Rad Laboratories, Inc.), the temperature of the well was increased by 0.5° C. from 30° C. up to 100° C. by a real-time PCR machine (CFX96 Touch Real-Time PCR System, manufactured by Bio-Rad Laboratories. Inc.), and following a lapse of 30 seconds after the target temperature was achieved, the fluorescence intensity of each well was measured simultaneously. SYPRO Orange was excited by a light emitting diode (LED) having a wavelength range of 450 to 490 nm, the SYPRO Orange emitted light was passed through a band pass filter of 560 to 580 nm range, the measurement of the fluorescence intensity was performed with a CCD camera, and changes in the fluorescence intensity were plotted as a function of temperature. The thermal denaturation temperature (melting temperature; Tm value) was defined as the local maximum value of the first derivative ("–d (Fluorescence)/dt" shown on the Y axis of the lower graph in FIG. 9) of the fluorescence intensity curve that is the function of temperature. The data analysis was carried out using the analysis software CFX Manager (manufactured by Bio-Rad Laboratories, Inc.) supplied with the real-time PCR machine.

Figure 9:
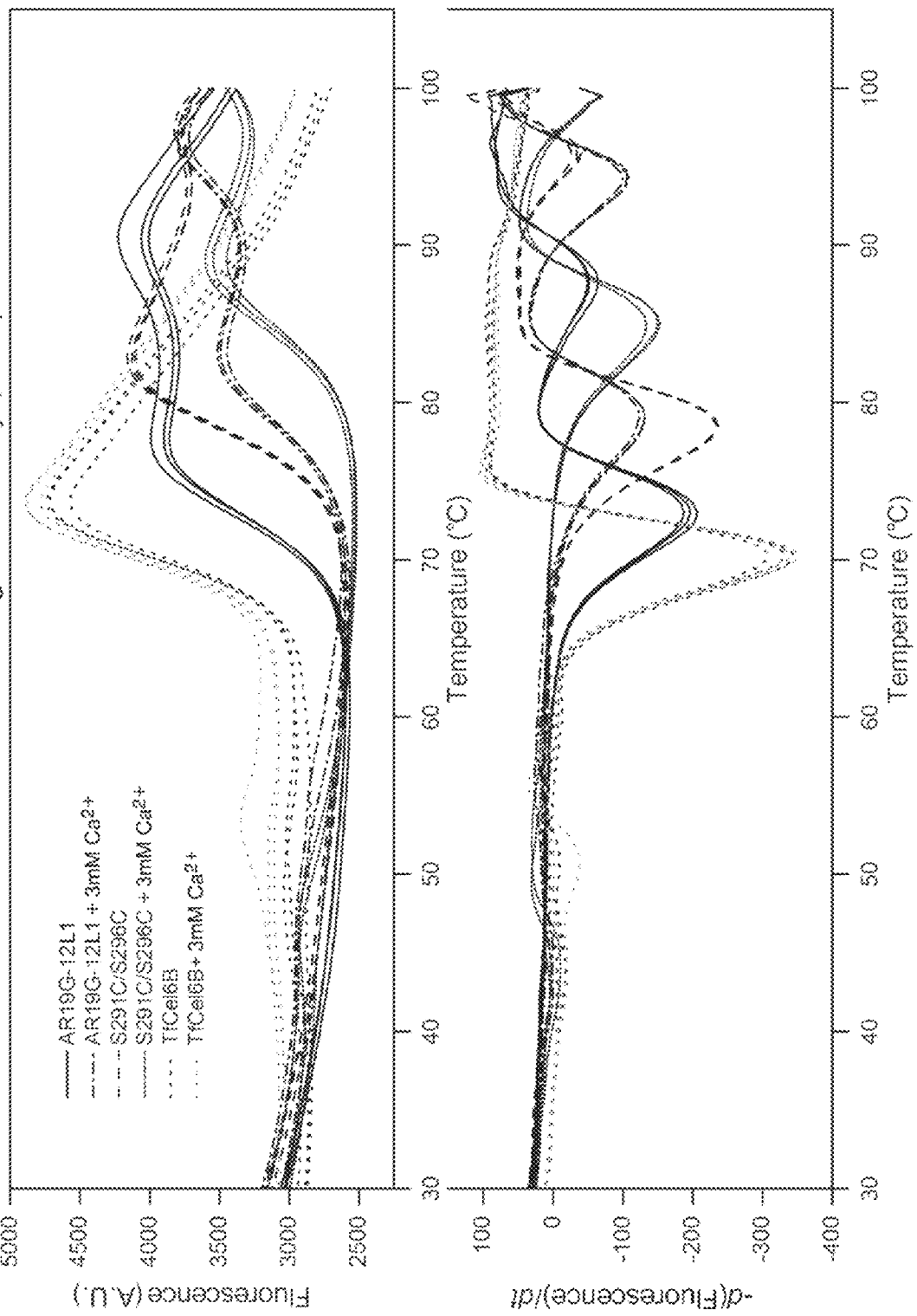
FIG. 9 is a diagram showing changes in the fluorescence intensity of SYPRO Orange caused in association with the thermal denaturation in Example 1 that were exhibited by each of the enzymatic proteins AR19G-12L1, the amino acid substituted variants S291C/S296C (indicated as "S291C/S296C" in the drawing) of AR19G-121, and a GH6 cellobiohydrolase TfCel6B derived from a thermophilic soil actinomycete *Thermobifida fusca*.

FIG. 9 shows changes in the fluorescence intensity of SYPRO Orange measured by the DSF method and caused in association with the thermal denaturation that were exhibited by each of the enzymatic proteins AR19G-12L1, the amino acid substituted variants S291C/S296C (indicated as "S291C/S296C" in the drawing) of AR19G-12L1, and a GH6 cellobiohydrolase TtCel6B derived from a thermophilic soil actinomycete *Thermobifida fusca*. The upper graph in FIG. 9 shows measured data, and the lower graph in FIG. 9 shows the first derivative "–d(Fluorescence)/dtf" of the fluorescence intensity change curve in the upper graph of FIG. 9.

The fluorescence intensity curve of AR19G-12L1 showed two peaks at around 78° C. and 90° C., suggesting that the thermal denaturation occurred in two stages. The first thermal denaturation showed a Tm value of 73.0±0.0 (n=3) (Table 2) which was close to the optimum temperature $T_{opt}$=70° C. of this enzyme obtained from the PSA hydrolytic activity. It was unclear for the second thermal denaturation.

The amino acid substituted variant S291C/S296C of AR19G-12L1 also showed two peaks in the same manner as the AR19G-12L1, and their peak temperatures were 83° C. and 97.5° C. The first thermal denaturation showed a Tm value of 78.5±0.0° C. (n=3) (Table 2), and the thermal stability was improved by 5.5° C. than the wild type by amino acid substitution. The optimum temperature $T_{opt}$ of the PSA hydrolytic activity of this enzyme was 75° C., which was roughly consistent with the Tm value measured by DSF. On the other hand, the fluorescence intensity curve of TfCel6B showed a single peak near 74° C., and the Tm value was 70.2±0.2° C. (n=3), which was 2.8° lower than that of AR19G-12L1 (Table 2). It should be noted that in Table 2, the thermal degradation temperature of each enzyme protein was independently measured three times by the DSF method, and the average values thereof are shown.

TABLE 2

| Enzyme | Melting temperature by DSF (° C., mean ± se) | |
|---|---|---|
| | First peak | Second peak |
| AR19G-12L1 | 73.0 ± 0.0 (n = 3) | 87.7 ± 0.2 (n = 3) |
| AR19G-12L1 + 3 mM Ca$^{2+}$ | 79.0 ± 0.0 (n = 3) | 99.3 ± 0.2 (n = 3) |
| S291C/S296C | 78.5 ± 0.0 (n = 3) | 95.8 ± 0.2 (n = 3) |
| S291C/S296C + 3 mM Ca$^{2+}$ | 85.0 ± 0.0 (n = 3) | 99.5 ± 0.0 (n = 3) |
| TfCel6B | 70.2 ± 0.2 (n = 3) | No |
| TfCel6B + 3 mM Ca$^{2+}$ | 70.5 ± 0.0 (n = 3) | No |

The Tm value of the amino acid substituted variant S291C/S296C of AR19G-12L1 was higher than that of AR19G-12 by 5.5° C. It was suggested that by replacing the amino acid residues at positions 291 and 296 of AR19G-12L1 with cysteine residues, both cysteine residues may form an SS bond to increase the thermal stability of the enzyme protein.

<14> Improvement of Thermal Stability of Enzyme Protein by Addition of Calcium Ions In general, divalent metal ions are known to stabilize the structure of the protein and improve the thermostability by binding to the protein. Therefore, the effects of calcium ions (concentration: 3 mM) on the Tm value of each enzyme were examined.

More specifically, 1 μL of the enzyme protein with a concentration of 1 mg/mL, 5 μL, of 200 mM acetate buffer (pH 5.5) and 12 μL of purified water or 5 mM calcium chloride solution were added into the wells of a 96-well PCR plate (Multiplate 96 Well PCR Plate MLL-9651, manufactured by Bio-Rad Laboratories, Inc.) and preincubated for 30 minutes at 30° C., and then 2 μL of 100-fold diluted SYPRO Orange (manufactured by Life Technologies Inc.) was added thereto, and the Tm values were measured in the same manner as in the above section <13> by the DSF method. The measurement results are shown in Table 2.

The Tm values of AR19G-12L1 and amino acid substituted variant S291C/S296C became 79.0±0.0° C. (n=3) and 85.0±0.0° C. (n=3), respectively, by the administration of calcium ions with a concentration of 3 mM. In other words, the Tm values were increased by the calcium ions by 5.5° C. in AR19G-12L1 and by 6.5° C. in S291C/S296C. On the other hand, GH6 cellobiohydrolase TfCel6B of the thermophilic soil actinomycete *Thermobifida fusca* did not improve the thermal stability by the addition of calcium ions, and the Tm value was 70.5=0.0° C. (n=3) (Table 2). This Tm value was lower than that of AR19G-121, added with calcium ions by 8.5° C. and was lower than that of the amino acid substituted variant S291C/S296C added with calcium ions by 14.5° C., respectively.

Example 2

As a means to produce the thermostable cellobiohydrolase according to the present invention in large quantities at a lower cost, the expression of the aforementioned protein in the actinomycete cells into which the AR19G-12L1 gene had been introduced was examined.

<1> Production of Actinomycete Cells Introduced with AR19G-12L1 Gene

The AR19G-12L1 gene cloned into the pET101/D-TOPO vector (manufactured by Life Technologies Inc.) was used as a template and transferred into an actinomycete expression vector pHSA81 (Japanese Unexamined Patent Application, First Publication No. 2007-53994) by PCR to be transformed into *Streptomyces lividans* TK24 strain. The transformation was carried out in accordance with the method (protoplast polyethylene glycol fusion method) described in "Genetic manipulation of *Streptomyces*: a laboratory manual". After the selection of positive clones by colony PCR and incubation in an YEME medium (0.3% yeast extract, 0.5% Bacto peptone, 0.3% malt extract, 1% glucose, 34% sucrose, 5 mM MgCl2, 0.5% glycine) with shaking, the recombinant plasmid was extracted and a sequence verification was performed using a 3730 DNA Analyzer sequencer (manufactured by Life Technologies Inc.).

<2> Expression of AR19G-12L1 Protein in Actinomycetes

The obtained transformant was inoculated into an YEME medium containing 5 μg/mL of thiostrepton and cultured for 5 days at 28° C. with shaking, and the cells were collected by centrifugation. The cells were washed in 50 mM Tris-HCl buffer (pH 8.0) and were then suspended by adding the same buffer of 1/10 volume of the culture medium. Then, a process of disrupting for 30 seconds with a sonication apparatus BioRuptorUCD-200T (manufactured by Cosmo Bio Inc.), followed by pausing for 30 seconds was carried out 10 times to obtain a supernatant after centrifugation (cell-free extract). A portion of the above cell-free extract was electrophoresed by SDS-PAGE to confirm the strong expression of the target protein of an expected size (46.5 kDa).

Figure 10:
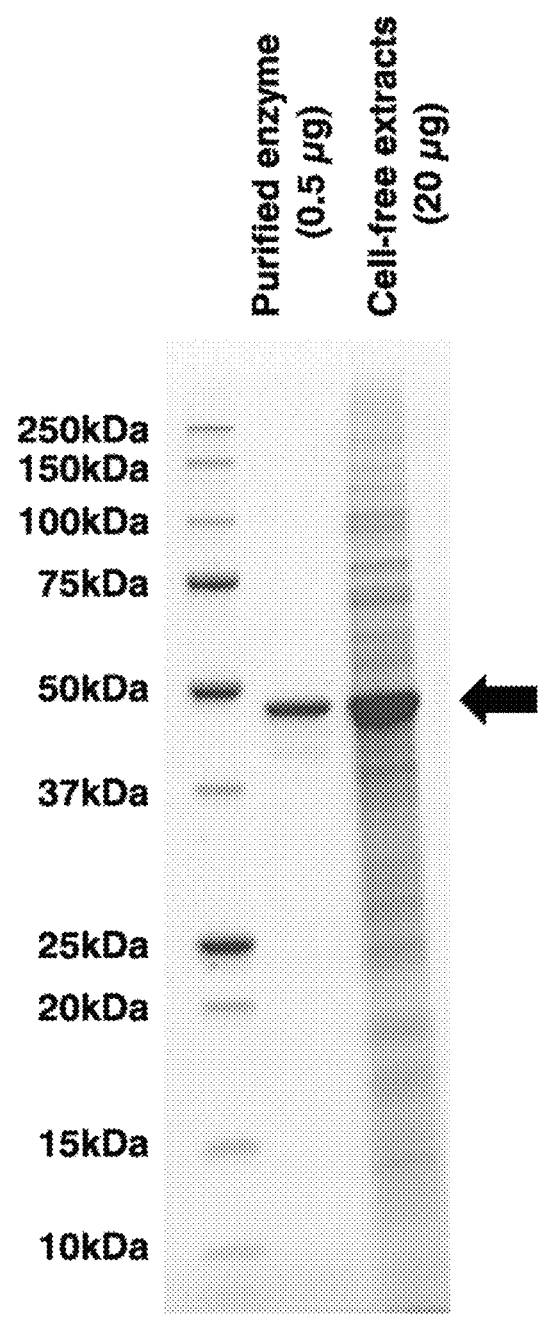
FIG. 10 is a diagram showing the result of an SDS-PAGE analysis of an AR19G-12L1, protein expressed in actinomycetes in Example 2.

The above cell-free extract and the purified enzyme sample solution obtained in the section <9> of Example 1 (*E. coli* expression control) were confirmed by SDS-PAGE analysis. The results of SDS-PAGE analysis of the cell-free extract (20 μg) of the transformed actinomycete cells introduced with the AR19G-12L1 gene and the purified enzyme sample solution (0.5 μg) are shown in FIG. 10. As a result, since a strong band was observed near a molecular weight of 46.5 kDa expected from the amino acid sequence (SEQ ID NO: 1) in the cell-free extract and a single band corresponding to the above band was observed in the purified enzyme sample solution, the AR19G-12L1 gene was confirmed to be expressed in actinomycete cells (indicated by arrows in the figure).

Figure 11:
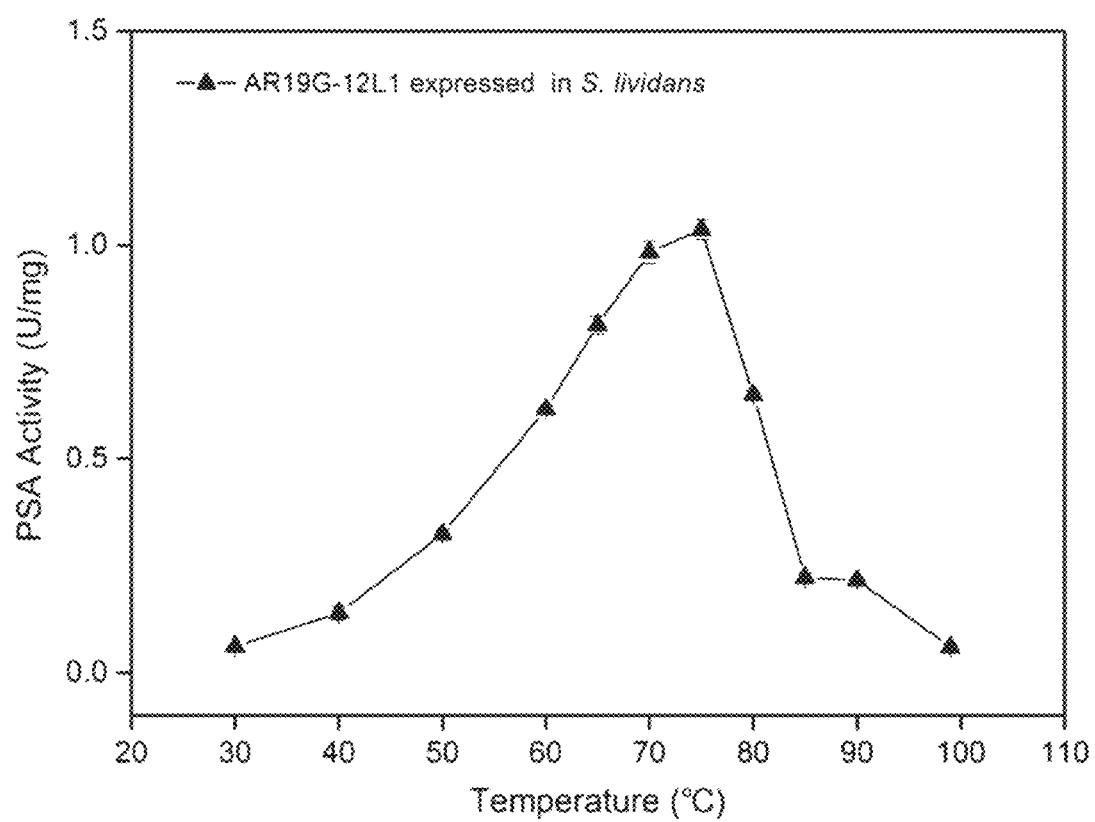
FIG. 11 is a diagram showing the measurement results of PSA hydrolytic activities at each temperature of the AR19G-12L1 protein expressed in actinomycetes in Example 2.

<3> Measurement of Enzyme Activity of AR19G-12L1 Protein Expressed in Actinomycete Cells The cellobiohydrolase activity was measured using a cell-free extract of the actinomycete cells transformed with the AR19G-12L1 gene. The activity measurement was carried out in the same manner as in the section <10> of Example 1 using a mixed solution composed of 50 μL of a cell-free extract sample, 50 μL of 200 mM acetate buffer (pH 5.5) and 100 μL of a 1% by mass PSA aqueous solution as a reaction solution. In all measurements, a mixed solution was used as a control which was prepared by reacting only 100 μL of a 1% by mass PSA aqueous solution at each temperature and adding thereto, after completion of the reaction, 50 μL of a cell-free extract sample and 50 μL of 200 mM acetate buffer (pH 5.5). Each measurement was carried out by three independent trials and the average value and the standard error were determined. The results are shown in FIG. 11. When the enzyme activity for producing 1 μmol of a reduced sugar per minute was defined as 1 U and the value obtained by division by the amount of enzyme protein (estimated from the result of SDS-PAGE) was defined as a specific activity (U/mg), the specific activity at 75° C. was 1.03 U/mg. As described above, since the AR19G-12 cellobiohydrolase enzyme showed satisfactory expression and activity also in actinomycete cells, it became clear that actinomycetes can be used as a host for gene transfer in order to express the thermostable cellobiohydrolase according to the present invention.

INDUSTRIAL APPLICABILITY

The thermostable cellobiohydrolase according to the present invention at least has a cellobiohydrolase activity under conditions of 75° C. and pH 5.5, and it is suitable for a hydrolysis process of cellulose-containing biomass under high temperature conditions of 75° C. or higher. Therefore, the aforementioned thermostable cellobiohydrolase and a polynucleotide used for the production thereof, an expression vector into which the aforementioned polynucleotide has been incorporated and a transformant into which the aforementioned expression vector has been introduced can be utilized, for example, in the field of energy production from the cellulose-containing biomass.

What is claimed is:

1. A thermostable cellobiohydrolase comprising:
(A) a polypeptide consisting of an amino acid sequence of SEQ ID NO: 1 or
(B) a polypeptide consisting of an amino acid sequence of SEQ ID NO: 3; and
at least one domain selected from the group consisting of a cellulose binding module, a linker domain, a signal peptide, and a tag.

2. A cellulase mixture comprising:
the thermostable cellobiohydrolase according to claim 1 and
at least one other cellulase.

* * * * *

SEQUENCE LISTING

```
<160> NUMBER OF SEQ ID NOS: 9

<210> SEQ ID NO 1
<211> LENGTH: 423
<212> TYPE: PRT
<213> ORGANISM: Unknown
<220> FEATURE:
<223> OTHER INFORMATION: AR19G-12L1

<400> SEQUENCE: 1

Leu Asp Asn Pro Phe Val Gly Ala Val Trp Tyr Val Asn Pro Asp Trp
  1               5                  10                  15

Ala Ala Asn Val Leu Asn Gln Ala Gln Gln Thr Gly Gly Thr Leu Gly
             20                  25                  30

Gln Arg Met Ala Ala Val Ala Gln Tyr Ser Thr Ala Val Trp Leu Asp
         35                  40                  45

Arg Ile Gly Ala Ile Thr Glu Gly Arg Gly Leu Gln Gly His Leu Asn
```

```
            50                  55                  60
Glu Ala Leu Ala Gln Gly Ala Asn Leu Ile Met Ile Val Ile Tyr Asp
 65                  70                  75                  80

Leu Pro Asn Arg Asp Cys Ala Ala Tyr Ala Ser Asn Gly Glu Leu Leu
                 85                  90                  95

Ile Ala Glu Asn Gly Leu Glu Arg Tyr Lys Arg Glu Tyr Ile Asp Val
            100                 105                 110

Ile Tyr Asn Ile Leu Ala Gln Pro Gln Tyr Arg Asn Leu Arg Ile Val
        115                 120                 125

Ala Val Ile Glu Pro Asp Ser Leu Pro Asn Leu Val Thr Asn Leu Ser
130                 135                 140

Glu Pro Ala Cys Ala Glu Ala Asn Ser Thr Gly Ala Tyr Val Glu Gly
145                 150                 155                 160

Ile Arg Tyr Ala Val Asn Lys Leu His Gln Leu Pro Asn Val Tyr Ile
                165                 170                 175

Tyr Leu Asp Ile Ala His Ser Gly Trp Leu Gly Trp Asp Asn Asn Phe
            180                 185                 190

Gln Gly Ala Val Asn Leu Tyr Thr Gln Val Val Gln Gly Met Ala Asp
        195                 200                 205

Gly Phe Asn Ser Ile Asp Gly Phe Val Thr Asn Thr Ala Asn Tyr Thr
210                 215                 220

Pro Val Glu Glu Pro Tyr Leu Pro Asp Pro Asn Leu Thr Ile Gly Gly
225                 230                 235                 240

Gln Pro Val Arg Ser Ala Asn Phe Tyr Glu Trp Asn Pro Tyr Phe Asp
                245                 250                 255

Glu Leu Asp Tyr Ala Gln Ala Leu Arg Gln Ala Phe Ile Gly Arg Gly
            260                 265                 270

Phe Pro Ser Gly Ile Gly Met Leu Ile Asp Thr Ser Arg Asn Gly Trp
        275                 280                 285

Gly Gly Ser Ser Tyr Gly Arg Ser Arg Pro Ser Gly Ala Ser Ser Asn
290                 295                 300

Thr Thr Asn Val Asn Val Tyr Val Asp Glu Ser Arg Val Asp Arg Arg
305                 310                 315                 320

Tyr His Arg Gly Asn Trp Cys Asn Gln Ala Gly Ile Gly Glu Arg
                325                 330                 335

Pro Arg Ala Asn Pro Ala Ala Gly Ile Asp Ala Tyr Val Trp Val Lys
            340                 345                 350

Pro Pro Gly Glu Ser Asp Gly Val Ser Gln Pro Gly Val Val Asp Pro
        355                 360                 365

Val Asp Pro Asn Lys Lys Phe Asp Ile Met Cys Asp Pro Asn Gly Gln
370                 375                 380

Ser Arg Tyr Asn Ser Ala Tyr Pro Thr Gly Ala Leu Pro Asn Ala Pro
385                 390                 395                 400

His Ala Gly Arg Trp Phe Pro Glu Gln Phe Glu Ile Leu Val Gln Asn
                405                 410                 415

Ala Tyr Pro Pro Ile Gln Pro
            420

<210> SEQ ID NO 2
<211> LENGTH: 1272
<212> TYPE: DNA
<213> ORGANISM: Unknown
<220> FEATURE:
<223> OTHER INFORMATION: AR19G-12L1
```

<400> SEQUENCE: 2

```
ctggacaacc cgtttgtggg ggcggtgtgg tacgtgaacc cggactgggc ggcgaatgtg    60
ctgaaccagg cgcagcagac agggggggacg ctggggcagc ggatggcggc ggtggcgcaa   120
tactcgacgg cggtgtggct ggaccggatc ggggcgatca cggaagggcg tggcttgcaa   180
gggcacctga acgaggcgct ggcgcaaggg gcgaacctga tcatgatcgt gatttacgat   240
ttgccgaacc gggactgtgc ggcatacgcg tcgaacgggg agttgctgat agcggagaac   300
gggctggagc ggtacaagag ggagtacata gatgtgatct acaacatttt ggcgcagccg   360
cagtaccgga atttgcggat cgtggcggtg atcgagccgg actcgctgcc gaacctggtg   420
acgaacctgt cggagccggc gtgtgcggag gcgaactcga cggggcgta tgtggaaggg   480
attcggtacg cggtgaacaa gctgcaccag ttgccgaacg tgtacatata tttggacata   540
gcgcattcgg ggtggttggg ctgggacaac aacttccagg gggcggtgaa cctgtacacg   600
caggtagtgc aggggatggc ggacgggttc aacagcatag acgggtttgt gacgaacacg   660
gcgaactaca cgccggtgga agagccgtac ctgccggacc cgaacctgac gatcggtggg   720
cagccggtgc ggtcggcgaa cttttacgag tggaacccgt actttgacga gctggactac   780
gcgcaggcgt tgcggcaggc gttcatcggg cggggctttc cgagcgggat agggatgctg   840
atcgacacga ccggaacgg gtggggcgga tcgagctatg gtcggagccg gccgagtggg   900
gcgagcagca acacgacgaa cgtgaacgtg tacgtgacg agtcgcgggt ggaccggcgg   960
tatcaccggg ggaactggtg caaccaggct gggggtatag gcgagcggcc gcgtgcgaac  1020
ccggcggccg ggatagatgc gtacgtgtgg gtgaagccgc ctggggagtc ggacggggtg  1080
agccaacctg gggtggtcga cccggtggat ccgaacaaga agtttgacat catgtgcgat  1140
ccgaacgggg agagccggta caactcggcg tatccgacgg gggcgttgcc gaacgcgccg  1200
cacgcggggc ggtggttccc ggagcagttt gagattctgg tgcagaacgc gtatccgccg  1260
attcagccgt aa                                                     1272
```

<210> SEQ ID NO 3
<211> LENGTH: 423
<212> TYPE: PRT
<213> ORGANISM: Unknown
<220> FEATURE:
<223> OTHER INFORMATION: AR19G-12L1-S291C/S296C

<400> SEQUENCE: 3

```
Leu Asp Asn Pro Phe Val Gly Ala Val Trp Tyr Val Asn Pro Asp Trp
  1               5                  10                  15

Ala Ala Asn Val Leu Asn Gln Ala Gln Gln Thr Gly Gly Thr Leu Gly
                 20                  25                  30

Gln Arg Met Ala Ala Val Ala Gln Tyr Ser Thr Ala Val Trp Leu Asp
             35                  40                  45

Arg Ile Gly Ala Ile Thr Glu Gly Arg Gly Leu Gln Gly His Leu Asn
         50                  55                  60

Glu Ala Leu Ala Gln Gly Ala Asn Leu Ile Met Ile Val Ile Tyr Asp
 65                  70                  75                  80

Leu Pro Asn Arg Asp Cys Ala Ala Tyr Ala Ser Asn Gly Glu Leu Leu
                 85                  90                  95

Ile Ala Glu Asn Gly Leu Glu Arg Tyr Lys Arg Glu Tyr Ile Asp Val
            100                 105                 110

Ile Tyr Asn Ile Leu Ala Gln Pro Gln Tyr Arg Asn Leu Arg Ile Val
        115                 120                 125
```

```
Ala Val Ile Glu Pro Asp Ser Leu Pro Asn Leu Val Thr Asn Leu Ser
    130                 135                 140

Glu Pro Ala Cys Ala Glu Ala Asn Ser Thr Gly Ala Tyr Val Glu Gly
145                 150                 155                 160

Ile Arg Tyr Ala Val Asn Lys Leu His Gln Leu Pro Asn Val Tyr Ile
                165                 170                 175

Tyr Leu Asp Ile Ala His Ser Gly Trp Leu Gly Trp Asp Asn Asn Phe
            180                 185                 190

Gln Gly Ala Val Asn Leu Tyr Thr Gln Val Val Gln Gly Met Ala Asp
        195                 200                 205

Gly Phe Asn Ser Ile Asp Gly Phe Val Thr Asn Thr Ala Asn Tyr Thr
    210                 215                 220

Pro Val Glu Glu Pro Tyr Leu Pro Asp Pro Asn Leu Thr Ile Gly Gly
225                 230                 235                 240

Gln Pro Val Arg Ser Ala Asn Phe Tyr Glu Trp Asn Pro Tyr Phe Asp
                245                 250                 255

Glu Leu Asp Tyr Ala Gln Ala Leu Arg Gln Ala Phe Ile Gly Arg Gly
            260                 265                 270

Phe Pro Ser Gly Ile Gly Met Leu Ile Asp Thr Ser Arg Asn Gly Trp
        275                 280                 285

Gly Gly Cys Ser Tyr Gly Arg Cys Arg Pro Ser Gly Ala Ser Ser Asn
    290                 295                 300

Thr Thr Asn Val Asn Val Tyr Val Asp Glu Ser Arg Val Asp Arg Arg
305                 310                 315                 320

Tyr His Arg Gly Asn Trp Cys Asn Gln Ala Gly Gly Ile Gly Glu Arg
                325                 330                 335

Pro Arg Ala Asn Pro Ala Ala Gly Ile Asp Ala Tyr Val Trp Val Lys
            340                 345                 350

Pro Pro Gly Glu Ser Asp Gly Val Ser Gln Pro Gly Val Val Asp Pro
        355                 360                 365

Val Asp Pro Asn Lys Lys Phe Asp Ile Met Cys Asp Pro Asn Gly Gln
    370                 375                 380

Ser Arg Tyr Asn Ser Ala Tyr Pro Thr Gly Ala Leu Pro Asn Ala Pro
385                 390                 395                 400

His Ala Gly Arg Trp Phe Pro Glu Gln Phe Glu Ile Leu Val Gln Asn
                405                 410                 415

Ala Tyr Pro Pro Ile Gln Pro
            420

<210> SEQ ID NO 4
<211> LENGTH: 1272
<212> TYPE: DNA
<213> ORGANISM: Unknown
<220> FEATURE:
<223> OTHER INFORMATION: AR19G-12L1-S291C/S296C

<400> SEQUENCE: 4
ctggacaacc cgtttgtggg ggcggtgtgg tacgtgaacc cggactgggc ggcgaatgtg    60
ctgaaccagg cgcagcagac aggggggacg ctggggcagc ggatggcggc ggtgcgcaa   120 tactcgacgg cggtgtggct ggaccggatc ggggcgatca cggaagggcg tggcttgcaa   180
gggcacctga cgaggcgct  ggcgcaaggg gcgaacctga tcatgatcgt gatttacgat   240
ttgccgaacc gggactgtgc ggcatacgcg tcgaacgggg agttgctgat agcggagaac   300
gggctggagc ggtacaagag ggagtacata gatgtgatct acaacatttt ggcgcagccg   360
```

```
cagtaccgga atttgcggat cgtggcggtg atcgagccgg actcgctgcc gaacctggtg      420
acgaacctgt cggagccggc gtgtgcgagg cgaactcga cggggggcgta tgtggaaggg      480 attcggtacg cggtgaacaa gctgcaccag ttgccgaacg tgtacatata tttggacata      540
gcgcattcgg ggtggttggg ctgggacaac aacttccagg gggcggtgaa cctgtacacg      600
caggtagtgc aggggatggc ggacgggttc aacagcatag acgggtttgt gacgaacacg      660
gcgaactaca cgccggtgga agagccgtac ctgccggacc cgaacctgac gatcggtggg      720
cagccggtgc ggtcggcgaa cttttacgag tggaacccgt actttgacga gctggactac      780
gcgcaggcgt tgcggcaggc gttcatcggg cggggctttc cgagcgggat agggatgctg      840
atcgacacga gccggaacgg gtggggcgga tgcagctatg gtcggtgccg gccgagtggg      900
gcgagcagca acacgacgaa cgtgaacgtg tacgtggacg agtcgcgggt ggaccggcgg      960
tatcaccggg ggaactggtg caaccaggct gggggtatag gcgagcggcc gcgtgcgaac     1020
ccggcggccg ggatagatgc gtacgtgtgg gtgaagccgc tgggggagtc ggacggggtg     1080
agccaacctg gggtggtcga cccggtggat ccgaacaaga agtttgacat catgtgcgat     1140
ccgaacgggc agagccggta caactcggcg tatccgacgg gggcgttgcc gaacgcgccg     1200
cacgcggggc ggtggttccc ggagcagttt gagattctgg tgcagaacgc gtatccgccg     1260
attcagccgt aa                                                         1272

<210> SEQ ID NO 5
<211> LENGTH: 474
<212> TYPE: PRT
<213> ORGANISM: Unknown
<220> FEATURE:
<223> OTHER INFORMATION: Amino acid sequence deduced from Open reading
      frame AR19G-166

<400> SEQUENCE: 5

Pro Thr Arg Thr Pro Thr Pro Ala Ala Pro Thr Ala Thr Pro Thr Pro
  1               5                  10                  15

Val Ala Pro Thr Ala Thr Pro Thr Arg Thr Pro Thr Pro Thr Leu Thr
                 20                  25                  30

Ser Thr Pro Gly Pro Thr Pro Thr Pro Pro Ser Gly Thr His Leu
             35                  40                  45

Asp Asn Pro Phe Ile Gly Ala Ile Gly Tyr Val Asn Pro Asp Trp Ala
         50                  55                  60

Thr Asn Val Ile Ser Gln Ala Asn Gln Thr Ala Asp Pro Thr Leu Ala
 65                  70                  75                  80

Ala Gln Met Arg Lys Val Ala Thr Tyr Ser Thr Ala Val Trp Leu Asp
                 85                  90                  95

Arg Ile Ala Ala Ile Thr Ala Gly Arg Gly Leu Arg Gly His Leu Asp
            100                 105                 110

Glu Ala Leu Arg Gln Met Gln Gln Ala Gly Gln Pro Val Val Ile Thr
            115                 120                 125

Leu Val Ile Tyr Asp Leu Pro Asn Arg Asp Cys Ser Ala Ala Ala Ser
        130                 135                 140

Asn Gly Glu Leu Leu Val Ala Gln Asn Gly Leu Ala Arg Tyr Lys Ala
145                 150                 155                 160

Glu Phe Ile Asp Pro Ile Val Ala Ile Leu Ser Asp Pro Arg Tyr Ala
                165                 170                 175

Gly Leu Arg Ile Val Thr Ile Ile Glu Pro Asp Ser Leu Pro Asn Leu
            180                 185                 190
```

```
Val Thr Asn Leu Ser Ile Pro Ala Cys Ala Glu Ala Gln Asn Ala Tyr
            195                 200                 205

Ile Glu Gly Ile Arg Tyr Ala Val Asn Arg Leu Arg Thr Ile Pro Asn
210                 215                 220

Val Tyr Ile Tyr Leu Asp Ile Ala His Ser Gly Trp Leu Gly Trp Asp
225                 230                 235                 240

Asn Asn Phe Asn Gly Ala Val Asn Leu Tyr Thr Gln Val Val Gln Gly
            245                 250                 255

Met Asp Gln Gly Phe Asn Ser Ile Asp Gly Phe Ile Thr Asn Val Ala
            260                 265                 270

Asn Tyr Thr Pro Leu Glu Glu Pro Tyr Leu Pro Asp Pro Asn Leu Thr
            275                 280                 285

Ile Ala Gly Gln Pro Val Arg Ser Ala Ser Phe Tyr Glu Trp Asn Pro
290                 295                 300

Tyr Phe Asp Glu Leu Asp Tyr Ala Leu Ala Leu Arg Asn Ala Phe Ile
305                 310                 315                 320

Gly Arg Gly Phe Pro Ser Thr Ile Gly Met Leu Ile Asp Thr Ser Arg
                325                 330                 335

Asn Gly Trp Gly Gly Cys Ser Tyr Gly Gln Cys Arg Pro Thr Gly Pro
            340                 345                 350

Ser Ser Asp Thr Ser Ser Val Asn Ala Tyr Val Asp Gly Ser Arg Val
            355                 360                 365

Asp Arg Arg Tyr His Arg Gly Asn Trp Cys Asn Gln Ala Gly Gly Ile
            370                 375                 380

Gly Glu Arg Pro Gln Ala Ala Pro Arg Ser Gly Ile Asp Ala Tyr Val
385                 390                 395                 400

Trp Val Lys Pro Gly Glu Ser Asp Gly Val Ser Gln Pro Gly Ile
                405                 410                 415

Val Asp Pro Asp Asp Pro Asn Lys Lys Phe Asp Pro Met Cys Asp Pro
            420                 425                 430

Asn Gly Gln Ser Arg Tyr Asn Ser Ala Tyr Pro Thr Gly Ala Leu Pro
            435                 440                 445

Asn Ala Pro His Ala Gly Arg Trp Phe Pro Gln Phe Glu Ile Leu
            450                 455                 460

Val Arg Asn Ala Tyr Pro Pro Ile Gln Pro
465                 470

<210> SEQ ID NO 6
<211> LENGTH: 427
<212> TYPE: PRT
<213> ORGANISM: Unknown
<220> FEATURE:
<223> OTHER INFORMATION: GH6 catalytic domain of AR19G-166RA

<400> SEQUENCE: 6

Leu Asp Asn Pro Phe Ile Gly Ala Ile Gly Tyr Val Asn Pro Asp Trp
1               5                   10                  15

Ala Thr Asn Val Ile Ser Gln Ala Asn Gln Thr Ala Asp Pro Thr Leu
                20                  25                  30

Ala Ala Gln Met Arg Lys Val Thr Tyr Ser Thr Ala Val Trp Leu
            35                  40                  45

Asp Arg Ile Ala Ala Ile Thr Ala Gly Arg Gly Leu Arg Gly His Leu
    50                  55                  60

Asp Glu Ala Leu Arg Gln Met Gln Gln Ala Gly Gln Pro Val Val Ile
65                  70                  75                  80
```

-continued

```
Thr Leu Val Ile Tyr Asp Leu Pro Asn Arg Asp Cys Ser Ala Ala Ala
                85                  90                  95

Ser Asn Gly Glu Leu Leu Val Ala Gln Asn Gly Leu Ala Arg Tyr Lys
            100                 105                 110

Ala Glu Phe Ile Asp Pro Ile Val Ala Ile Leu Ser Asp Pro Arg Tyr
        115                 120                 125

Ala Gly Leu Arg Ile Val Thr Ile Ile Glu Pro Asp Ser Leu Pro Asn
130                 135                 140

Leu Val Thr Asn Leu Ser Ile Pro Ala Cys Ala Glu Ala Gln Asn Ala
145                 150                 155                 160

Tyr Ile Glu Gly Ile Arg Tyr Ala Val Asn Arg Leu Arg Thr Ile Pro
                165                 170                 175

Asn Val Tyr Ile Tyr Leu Asp Ile Ala His Ser Gly Trp Leu Gly Trp
            180                 185                 190

Asp Asn Asn Phe Asn Gly Ala Val Asn Leu Tyr Thr Gln Val Val Gln
        195                 200                 205

Gly Met Asp Gln Gly Phe Asn Ser Ile Asp Gly Phe Ile Thr Asn Val
210                 215                 220

Ala Asn Tyr Thr Pro Leu Glu Glu Pro Tyr Leu Pro Asp Pro Asn Leu
225                 230                 235                 240

Thr Ile Ala Gly Gln Pro Val Arg Ser Ala Ser Phe Tyr Glu Trp Asn
                245                 250                 255

Pro Tyr Phe Asp Glu Leu Asp Tyr Ala Leu Ala Leu Arg Asn Ala Phe
            260                 265                 270

Ile Gly Arg Gly Phe Pro Ser Thr Ile Gly Met Leu Ile Asp Thr Ser
        275                 280                 285

Arg Asn Gly Trp Gly Gly Cys Ser Tyr Gly Arg Cys Arg Pro Thr Gly
290                 295                 300

Pro Ser Ser Asp Thr Ser Ser Val Asn Ala Tyr Val Asp Gly Ser Arg
305                 310                 315                 320

Val Asp Arg Arg Tyr His Arg Gly Asn Trp Cys Asn Gln Ala Gly Gly
                325                 330                 335

Ile Gly Glu Arg Pro Gln Ala Ala Pro Arg Ser Gly Ile Asp Ala Tyr
            340                 345                 350

Val Trp Val Lys Pro Pro Gly Glu Ser Asp Gly Val Ser Gln Pro Gly
        355                 360                 365

Ile Val Asp Pro Asp Pro Asn Lys Lys Phe Asp Pro Met Cys Asp
        370                 375                 380

Pro Asn Gly Gln Ser Arg Tyr Asn Ser Ala Tyr Pro Thr Gly Ala Leu
385                 390                 395                 400

Pro Asn Ala Pro His Ala Gly Arg Trp Phe Pro Gln Gln Phe Glu Ile
                405                 410                 415

Leu Val Arg Asn Ala Tyr Pro Pro Ile Gln Pro
            420                 425
```

<210> SEQ ID NO 7
<211> LENGTH: 459
<212> TYPE: PRT
<213> ORGANISM: Unknown
<220> FEATURE:
<223> OTHER INFORMATION: Amino acid sequence deduced from Open reading
      frame AR19G-12

<400> SEQUENCE: 7

Thr Ala Thr Pro Thr Arg Thr Pro Thr Pro Pro Ala Gln Pro Thr Ala

```
                1               5                    10                   15
            Thr Pro Thr Arg Thr Pro Thr Pro Thr Ala Val Ala Pro Thr Pro Val
                            20                  25                  30
            Pro Gly Val His Leu Asp Asn Pro Phe Val Gly Ala Val Trp Tyr Val
                            35                  40                  45
            Asn Pro Asp Trp Ala Ala Asn Val Leu Asn Gln Ala Gln Gln Thr Gly
                            50                  55                  60
            Gly Thr Leu Gly Gln Arg Met Ala Ala Val Ala Gln Tyr Ser Thr Ala
             65                 70                  75                  80
            Val Trp Leu Asp Arg Ile Gly Ala Ile Thr Glu Gly Arg Gly Leu Gln
                            85                  90                  95
            Gly His Leu Asn Glu Ala Leu Ala Gln Gly Ala Asn Leu Ile Met Ile
                            100                 105                 110
            Val Ile Tyr Asp Leu Pro Asn Arg Asp Cys Ala Ala Tyr Ala Ser Asn
                            115                 120                 125
            Gly Glu Leu Leu Ile Ala Glu Asn Gly Leu Glu Arg Tyr Lys Arg Glu
                            130                 135                 140
            Tyr Ile Asp Val Ile Tyr Asn Ile Leu Ala Gln Pro Gln Tyr Arg Asn
            145                 150                 155                 160
            Leu Arg Ile Val Ala Val Ile Glu Pro Asp Ser Leu Pro Asn Leu Val
                            165                 170                 175
            Thr Asn Leu Ser Glu Pro Ala Cys Ala Glu Ala Asn Ser Thr Gly Ala
                            180                 185                 190
            Tyr Val Glu Gly Ile Arg Tyr Ala Val Asn Lys Leu His Gln Leu Pro
                            195                 200                 205
            Asn Val Tyr Ile Tyr Leu Asp Ile Ala His Ser Gly Trp Leu Gly Trp
                            210                 215                 220
            Asp Asn Asn Phe Gln Gly Ala Val Asn Leu Tyr Thr Gln Val Val Gln
            225                 230                 235                 240
            Gly Met Ala Asp Gly Phe Asn Ser Ile Asp Gly Phe Val Thr Asn Thr
                            245                 250                 255
            Ala Asn Tyr Thr Pro Val Glu Glu Pro Tyr Leu Pro Asp Pro Asn Leu
                            260                 265                 270
            Thr Ile Gly Gly Gln Pro Val Arg Ser Ala Asn Phe Tyr Glu Trp Asn
                            275                 280                 285
            Pro Tyr Phe Asp Glu Leu Asp Tyr Ala Gln Ala Leu Arg Gln Ala Phe
                            290                 295                 300
            Ile Gly Arg Gly Phe Pro Ser Gly Ile Gly Met Leu Ile Asp Thr Ser
            305                 310                 315                 320
            Arg Asn Gly Trp Gly Gly Ser Ser Tyr Gly Arg Ser Arg Pro Ser Gly
                            325                 330                 335
            Ala Ser Ser Asn Thr Thr Asn Val Val Tyr Val Asp Glu Ser Arg
                            340                 345                 350
            Val Asp Arg Arg Tyr His Arg Gly Asn Trp Cys Asn Gln Ala Gly Gly
                            355                 360                 365
            Ile Gly Glu Arg Pro Arg Ala Asn Pro Ala Ala Gly Ile Asp Ala Tyr
                            370                 375                 380
            Val Trp Val Lys Pro Pro Gly Glu Ser Asp Gly Val Ser Gln Pro Gly
            385                 390                 395                 400
            Val Val Asp Pro Val Asp Pro Asn Lys Lys Phe Asp Ile Met Cys Asp
                            405                 410                 415
            Pro Asn Gly Gln Ser Arg Tyr Asn Ser Ala Tyr Pro Thr Gly Ala Leu
                            420                 425                 430
```

Pro Asn Ala Pro His Ala Gly Arg Trp Phe Pro Glu Gln Phe Glu Ile
            435                 440                 445

Leu Val Gln Asn Ala Tyr Pro Pro Ile Gln Pro
    450                 455

<210> SEQ ID NO 8
<211> LENGTH: 430
<212> TYPE: PRT
<213> ORGANISM: Herpetosiphon aurantiacus DSM 785
<220> FEATURE:
<223> OTHER INFORMATION: Catalytic domain of glycoside hydrolase
      family 6

<400> SEQUENCE: 8

His Val Ala Asn Pro Phe Val Gly Ala Gln Gly Tyr Ile Asn Ser Glu
  1               5                  10                  15

Tyr Ala Ala Arg Val Asn Ala Glu Ala Asn Ala Thr Gly Gly Thr Leu
                 20                  25                  30

Gly Ser Gln Met Arg Gln Val Ala Ser Tyr Pro Thr Ala Val Trp Leu
             35                  40                  45

Asp Arg Ile Ala Ala Ile Ala Gly Ser Ser Glu Ser Met Gly Leu Arg
         50                  55                  60

Ala His Leu Asp Ala Ala Leu Val Gln Gln Thr Ser Gly Gln Gln
 65                  70                  75                  80

Val Ala Ile Ser Ile Val Val Tyr Asp Leu Pro Asn Arg Asp Cys Ala
                 85                  90                  95

Ala Leu Ala Ser Asn Gly Glu Leu Lys Ile Ser Glu Asn Gly Leu Asn
            100                 105                 110

Arg Tyr Lys Thr Glu Tyr Ile Asp Pro Ile Ala Ala Ile Val Gly Glu
        115                 120                 125

Ser Lys Tyr Ala Ser Leu Arg Ile Val Val Ile Leu Glu Pro Asp Ser
    130                 135                 140

Leu Ser Asn Leu Val Thr Asn Ala Ser Ile Pro Ala Cys Ala Glu Ala
145                 150                 155                 160

Ile Ser Ser Gly Ala Tyr Val Gln Gly Val Gln Tyr Ala Ile Asn Lys
                165                 170                 175

Leu Asn Val Thr Ser Asn Val Tyr Ile Tyr Met Asp Ile Ala His Ser
            180                 185                 190

Gly Trp Leu Gly Trp Asp Ser Asn Phe Thr Pro Ala Ile Gln Leu Tyr
        195                 200                 205

Thr Gln Thr Val Arg Gly Thr Thr Lys Gly Leu Asn Gly Ile Asp Gly
    210                 215                 220

Phe Ile Ser Asn Thr Ala Asn Tyr Thr Pro Leu Asn Glu Val Phe Leu
225                 230                 235                 240

Pro Asn Ser Gly Leu Thr Leu Gly Gly Asn Pro Ile Arg Ser Ser
                245                 250                 255

Leu Phe Tyr Glu Trp Asn Pro Tyr Phe Asp Glu Thr Asp Tyr Val Leu
            260                 265                 270

Ala Met Arg Asn Ala Phe Ile Thr Ala Gly Phe Pro Ser Gly Ile Gly
        275                 280                 285

Met Leu Ile Asp Thr Ser Arg Asn Gly Trp Gly Thr Ala Arg Pro
    290                 295                 300

Thr Met Val Ser Ser Ser Asn Ser Leu Glu Ile Tyr Val Asn Asp Ser
305                 310                 315                 320

Lys Leu Asp Arg Arg Pro His Arg Gly Gly Trp Cys Asn Gln Ala Gly

```
                        325                 330                 335
Ala Gly Ile Gly Glu Arg Pro Thr Ala Ala Pro Val Ser Gly Ile Asp
                340                 345                 350
Ala Tyr Val Trp Val Lys Pro Gly Glu Ser Asp Gly Val Ala Thr
            355                 360                 365
Ala Gly Val Ile Asp Pro Thr Asp Pro Ala Lys Gln Phe Asp Ala Met
        370                 375                 380
Cys Asp Pro Asn Ala Gln Asn Arg Tyr Asn Thr Ala Tyr Pro Thr Asn
385                 390                 395                 400
Ala Leu Ala Gly Ala Pro His Ala Gly Arg Trp Phe Pro Ser Gln Phe
                405                 410                 415
Ala Met Leu Val Arg Asn Ala Tyr Pro Pro Ile Ser Gln Ser
                420                 425                 430

<210> SEQ ID NO 9
<211> LENGTH: 420
<212> TYPE: PRT
<213> ORGANISM: Thermobifida fusca
<220> FEATURE:
<223> OTHER INFORMATION: Catalytic domain of TfCel6B (glycoside
      hydrolase family 6)

<400> SEQUENCE: 9

Glu Lys Val Asp Asn Pro Phe Glu Gly Ala Lys Leu Tyr Val Asn Pro
1               5                   10                  15
Val Trp Ser Ala Lys Ala Ala Glu Pro Gly Gly Ser Ala Val Ala
            20                  25                  30
Asn Glu Ser Thr Ala Val Trp Leu Asp Arg Ile Gly Ala Ile Glu Gly
        35                  40                  45
Asn Asp Ser Pro Thr Thr Gly Ser Met Gly Leu Arg Asp His Leu Glu
    50                  55                  60
Glu Ala Val Arg Gln Ser Gly Gly Asp Pro Leu Thr Ile Gln Val Val
65                  70                  75                  80
Ile Tyr Asn Leu Pro Gly Arg Asp Cys Ala Ala Leu Ala Ser Asn Gly
                85                  90                  95
Glu Leu Gly Pro Asp Glu Leu Asp Arg Tyr Lys Ser Glu Tyr Ile Asp
            100                 105                 110
Pro Ile Ala Asp Ile Met Trp Asp Phe Ala Asp Tyr Glu Asn Leu Arg
        115                 120                 125
Ile Val Ala Ile Ile Glu Ile Asp Ser Leu Pro Asn Leu Val Thr Asn
    130                 135                 140
Val Gly Gly Asn Gly Gly Thr Glu Leu Cys Ala Tyr Met Lys Gln Asn
145                 150                 155                 160
Gly Gly Tyr Val Asn Gly Val Gly Tyr Ala Leu Arg Lys Leu Gly Glu
                165                 170                 175
Ile Pro Asn Val Tyr Asn Tyr Ile Asp Ala Ala His His Gly Trp Ile
            180                 185                 190
Gly Trp Asp Ser Asn Phe Gly Pro Ser Val Asp Ile Phe Tyr Glu Ala
        195                 200                 205
Ala Asn Ala Ser Gly Ser Thr Val Asp Tyr Val His Gly Phe Ile Ser
    210                 215                 220
Asn Thr Ala Asn Tyr Ser Ala Thr Val Glu Pro Tyr Leu Asp Val Asn
225                 230                 235                 240
Gly Thr Val Asn Gly Gln Leu Ile Arg Gln Ser Lys Trp Val Asp Trp
                245                 250                 255
```

```
Asn Gln Tyr Val Asp Glu Leu Ser Phe Val Gln Asp Leu Arg Gln Ala
            260             265             270
Leu Ile Ala Lys Gly Phe Arg Ser Asp Ile Gly Met Leu Ile Asp Thr
            275             280             285
Ser Arg Asn Gly Trp Gly Gly Pro Asn Arg Pro Thr Gly Pro Ser Ser
            290             295             300
Ser Thr Asp Leu Asn Thr Tyr Val Asp Glu Ser Arg Ile Asp Arg Arg
305                 310             315                 320
Ile His Pro Gly Asn Trp Cys Asn Gln Ala Gly Ala Gly Leu Gly Glu
                325             330             335
Arg Pro Thr Val Asn Pro Ala Pro Gly Val Asp Ala Tyr Val Trp Val
            340             345             350
Lys Pro Pro Gly Glu Ser Asp Gly Ala Ser Glu Glu Ile Pro Asn Asp
            355             360             365
Glu Gly Lys Gly Phe Asp Arg Met Cys Asp Pro Thr Tyr Gln Gly Asn
            370             375             380
Ala Arg Asn Gly Asn Asn Pro Ser Gly Ala Leu Pro Asn Ala Pro Ile
385             390             395                 400
Ser Gly His Trp Phe Ser Ala Gln Phe Arg Glu Leu Leu Ala Asn Ala
                405             410             415
Tyr Pro Pro Leu
            420
```